United States Patent [19]
Kim

[11] Patent Number: 5,879,797
[45] Date of Patent: Mar. 9, 1999

[54] MATRIX WHICH CONTAINS NEPHRITE JADE POWDER AS A MAIN COMPONENT

[76] Inventor: Jun-Han Kim, #102-902 Hanjoo Apartment, Twaegye-dong 944, Choonchun-Shi, Kangwon-do, Rep. of Korea

[21] Appl. No.: 698,303

[22] Filed: Aug. 15, 1996

[51] Int. Cl.[6] .................................................. B32B 5/16
[52] U.S. Cl. .................. 428/328; 428/329; 428/330; 428/331; 428/332; 428/402; 428/432; 428/697; 428/701; 428/702
[58] Field of Search ..................... 428/402, 323, 428/331, 328, 329, 330, 332, 432, 428, 697, 701, 702

[56] References Cited

U.S. PATENT DOCUMENTS

| | | | |
|---|---|---|---|
| 4,809,417 | 3/1989 | Normann | 29/896.41 |
| 4,857,306 | 8/1989 | Roller | 424/63 |
| 5,154,607 | 10/1992 | Hanson | 433/8 |

FOREIGN PATENT DOCUMENTS

| | | |
|---|---|---|
| 19-636798 | 3/1998 | Germany . |
| 10-007915 | 1/1998 | Japan . |
| 10-088103 | 4/1998 | Japan . |

OTHER PUBLICATIONS

Kim, Won–sa, "Nephrite from Chuncheon, Korea"; J. Gemmol., 24(8), 547–50, 1995.

Lai et al, "Microstructure and Mechanical Properties of a Tough Natural Fibrous Ceramic, Nephrite", Mater. Sci. Forum, 34–36 (int. Ceram. Conf., Austceram 88, Pt. 1), 537–41, 1988.

Dorling et al, "An Investigation of Nephrite Jade by Electron Microscopy", Mineral Mag., 49(350), 31–36, 1985.

Mallinson et al, "The Internal Structure of Nephrite: Experimental and Computational Evidence for the Coexistence of Multiple–Chain Silicates Within an Amphibole Host", Philos. Trans. R. Soc. London, Ser. A, 295(1416), 537–52, 1980.

Hutchison et al, "Structural Irregularities in Nephrite Jade: An Electron Microscope Study", Mater. Res. Bull., 11(12), 1557–61, 1976.

*Primary Examiner*—H. Thi Le
*Attorney, Agent, or Firm*—Michael N. Meller

[57] ABSTRACT

The present invention relates to a novel matrix containing nephrite jade powder as a main component. By using the matrix, a variety of goods in the field of medical goods, utensil goods, equipments for leisure time, vessels, interior goods, agricultural goods, industrial goods, fishery goods, traffic goods, transportation goods, equipments for sports, electronic instruments, precision instrument, or the like can be prepared. The goods made of the matrix can show excellent effects of treating pathological symptoms (headache, numb feeling, indigestion, insomnia, or the like), removing impurities (such as heavy metals), improving the quality of water, promoting the growth of plants by virtue of the inherent properties of nephrite jade.

2 Claims, 14 Drawing Sheets

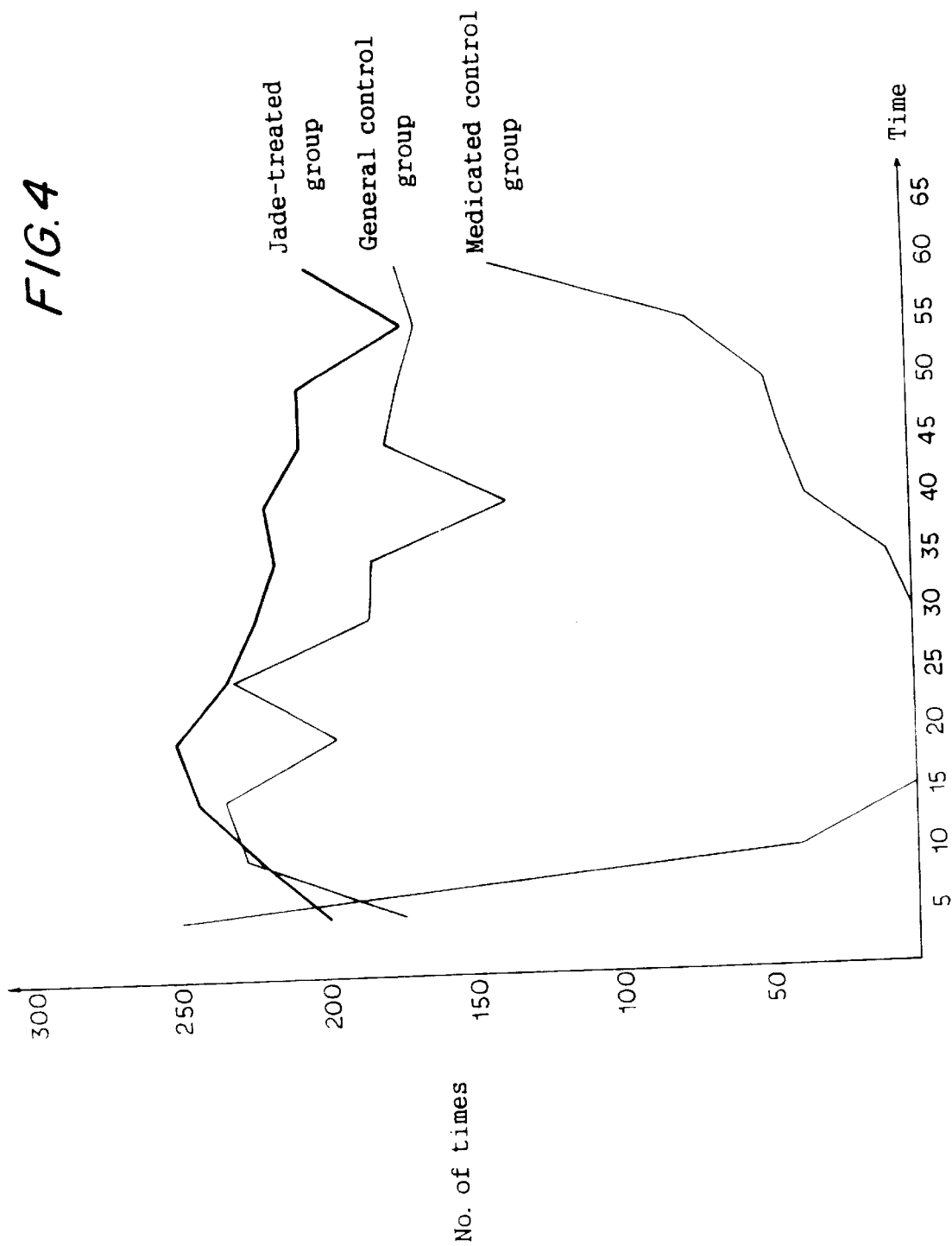

```
-- ELEMENT ; NI ==
----------------------------------------------------------------
( INSTRUMENT CONDITION )
HCL# (MA)   SLIT(NM)   WL(HH)    MODE
  8    4     0.15      232.0      (    )
----------------------------------------------------------------
( FLAME CONDITION )
FLAME       FUEL    OXIDANT    BURNER(CM)   H(HH)    e(DEG)
AIR-C2H2    1.7        8          10         (6)      (   )
----------------------------------------------------------------
ANALYTICAL LINE SEARCH 232.0 NM ; NI

88-FINISHED
----------------------------------------------------------------
( CONC CAL. METHOD )  ; NORMAL
STD         S1      S2      S3      S4      S5      S6
CONC         -       -       -       -       -       -
----------------------------------------------------------------
             5      10      50       -       -
            SPL#          ABS      CONC       8G       CV
           BLANK         .005

.082
           STD1          .082      5.000               .000
           BLANK       - .004

.190
           STD2          .190     10.00                .000
           BLANK       - .001

.395
           STD3          .395     50.00                .000
```

FIG.12

```
STD DATA OMIT
  1. OMIT;(OMIT)(DATA NO.) (E)(E)
  2. NOT OMIT; (E)(E)
CAL. CURVE READY
```

|     |         |       |      |
|-----|---------|-------|------|
|     | BLANK   | − .027 |     |
| 115 | .927 .927 | 51.80 | .000 |
|     | BLANK   | − .023 |     |
| 116 | .926 .926 | 51.75 | .000 |
|     | BLANK   | − .026 |     |
| 116 | .877 .877 | 48.92 | .000 |
|     | BLANK   | − .030 |     |
| 118 | .032 .032 | 1.733 | .000 |
|     | BLANK   | .029  |      |
| 119 | .922 .922 | 51.54 | .000 |

—▲— Jade Container    —○— Control

—△— Jade Container    —○— Control

MATRIX WHICH CONTAINS NEPHRITE JADE POWDER AS A MAIN COMPONENT

FIELD OF THE INVENTION

The present invention relates to a matrix containing fine powder of nephrite jade as a main component.

More specifically, the present invention relates to the matrix containing fine powder of nephrite jade of very fine combination weave fibrous microstructure of cryptocrystalline tremolite type. By using the matrix, a variety of goods in the field of medical goods, utensil goods, equipments for leisure time, vessels, interior goods, agricultural goods, industrial goods, fishery goods, traffic goods, transportation goods, equipments for sports, electronic instruments, precision instrument, or the like can be prepared. The goods made of the matrix can show excellent effects of treating pathological symptoms (headache, numb feeling, indigestion, insomnia, or the like), removing impurities (such as heavy metals), improving the quality of water, promoting the growth of plants by virtue of the inherent properties of nephrite jade.

PRIOR ARTS

As is generally known, jade is largely divided into jadeite and nephrite jade.

Jadeite belongs to pyroxene family and has monoclinic system comprising silicic acid, aluminum oxide and soda. It is an intimate mass, and the hardness is comparable to that of crystal. It is transparent or translucent of black, blue green or green color. People usually says the jadeite as "jade".

Nephrite jade is an inorganic material having monoclinic system of inosilicates. The quality of nephrite jade is determined by the fine structure, and the finer the fiber, the better is the quality.

According to a German literature [Mauda Palmer Die Verborgene, "KRAFF der KRISTALLE und der EDELSTEINE"], the two different ores, jadeite and nephrite jade, both comprises silicon and oxygen, as most of other jewels. However, Jadeite is formed of granular crystals while nephrite jade consists of lots of crystals and aggregates of microparticles having fibrous, hair-like structure. In particular, nephrite jade comprises three elements, Ca, Fe and Mg, which are good for human body, while jadeite comprises sodium and aluminum components. Thus, it has been recently reported that nephrite jade, when attached to the body, provides a considerable effect to the treatment of hypertension, diabetes, circulating system disorder, heart disease and kidney disorder.

A classic of traditional oriental medicine, "Treasures in oriental medicine" describes that if jade is added to black rice liquor to alter the liquor to water, and intake of jade powder in a size like sesame seed is good for the discharge of the waste material. Also it describes that when jade powder (1 part by volume), rice (1 part by volume) and white dew (1 part by volume) are cooked to rice in a copper vessel, the jade powder becomes water (so called jade-liquid, the "divine jade water"). "Plants of Divine Agriculture", "Plants of Tang Age" and "List of Basic Plants" describes that intake of jade powder in a size like sesame seed enriches five viscera and six entrails and completely discharges the waste materials. In addition, it is effective to digestive system by remove heat from stomach, and it is good for the treatment of bronchus asthma, body fever and heavy feeling in the chest as well as thirst. When jade powder is taken for a long time, body becomes easy and light, function of lung is enhanced, making voice by vocal cords becomes easier. Also, it is good for throat, nutrition of hair, functions of five viscera and six entrails and treatment of nervous diseases such as stress. Besides, the components of nephrite jade reveals excellent functions to the body without side effect. For example, intake of white jade powder is good for the tension or cramps in the muscles and rubbing with nephrite jade on the hurted skin for several days removes the scar.

However, as nephrite jade does not exists in a large amount in the nature, the use thereof is restricted to jewel personal ornaments such as necklace, ring, bracelet, or the like in spite of the well known excellent medical functions. In addition, the processing of nephrite jade requires delicate efforts of experts having much experiences, and nephrite jade is economically disadvantageous having very high price, so that the development as a general practical goods using nephrite jade are intensively needed.

SUMMARY OF THE INVENTION

The present inventors have paid attention to the excellent medical effects of nephrite jade and intensively studied for many years, and as a result, found the fact that the product (agricultural goods, industrial goods, fishery goods, medical goods, electronic products, precision instruments, civil engineering and construction) made of (or comprising) nephrite jade powder of cryptocrystalline tremolite of $\sigma^{18}O$ as an effective component by a conventional molding process provides activities of removing heavy metals, removing offensive odor, promoting the growth of plants, improving the quality of water as well as enhance the physical properties of the product itself, to complete the invention.

Thus, the object of the present invention is to provide a novel matrix having excellent medical and physical effects due to the inherent properties of nephrite jade (powder) when applied to utensil goods such as tableware, products for sports or leisure time, agricultural goods such as facility gardening, fishery goods such as fish box, traffic goods such as automobile components, transportation goods, film for food package, medical goods such as parts of spectacles, electronic instrument such as electric or electronic parts.

Another object of the present invention is to maximize the utilization of nephrite jade powder which is remainder or waste of the mining or minute processing of nephrite jade ornaments.

The other objects or advantages of the present invention can be clarified by the description of the specification and Examples here-in-below.

BRIEF DESCRIPTION OF THE DRAWINGS

FIG. 4 shows the effect of jade mug on sensory attributes of coffee.

FIG. 12 shows the output of the results of the analysis (Experimental Example 9).

DETAILED DESCRIPTION OF THE INVENTION

Figure 1:
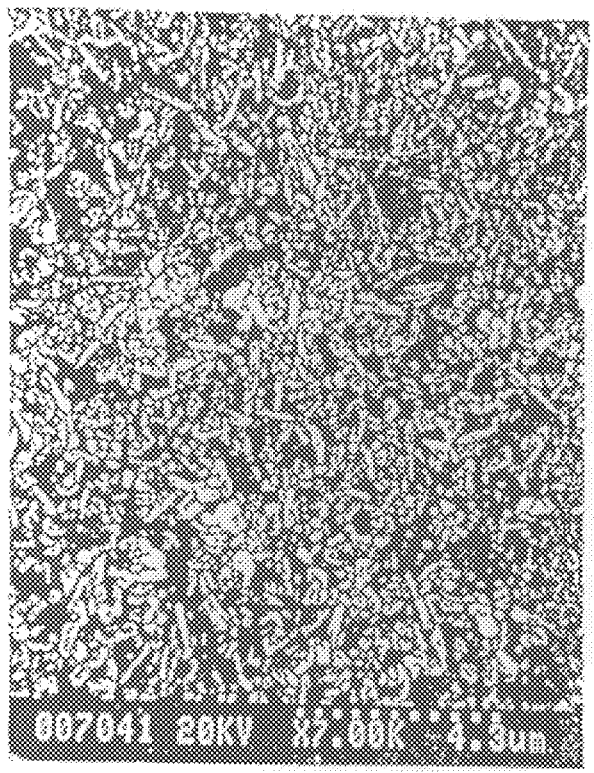
FIG. 1 is shows crystalline structure of a matrix according to the present invention by Scanning Electron Microscope (SEM).

According to the present invention, a variety of goods are made of a matrix containing 5–100% by weight of nephrite jade powder preferably having particle size of 100–350 mesh, by general molding process. The nephrite jade powder of the matrix has been homogeneously dispersed in the molded articles to exhibit the effects of nephrite jade as well as to enhance the physical properties of the articles.

In the present invention, each article may be a variety of non-restricted goods which requires the admixing of nephrite jade powder therein.

In the specification, though explanation is made by referring to plastic goods containing nephrite jade as a main current, it should be understood that the matrix of the present invention is never restricted to plastic materials.

The matrix may be in a form of powdery mixture, synthetic resin composition, synthetic glass or solid mass.

The thermoplastic synthetic resins as raw material of the plastic materials described in the specification includes polyvinyl chloride (PVC), polyvinyl acetate (PVAC), polyvinyl alcohol (PVA, PVAL), polyvinyl acetal, polyvinyl formal (PVFM), polyvinyl butyral (PVB), polyvinylidene chloride (PVDC), polyvinylidene chloride-polyvinyl chloride copolymer, polyethylene (PE), polypropylene (PP), polystyrene (PS), styrene-butadiene copolymer (SB, HIPS), polystyrene foam (EPS, FS), acrylonitrile-styrene copolymer (AS, SAN), acrylonitrile-butadiene-styrene copolymer (ABS), ethylene-vinyl acetate copolymer (EVA), ionomer, polycarbonate (PC), polyvinyl ether-polyvinyl methyl ether, polyvinyl ketone, polytetrafluoroethylene (PTFE), polytrifluorochloroethylene (PCTFE), polyvinyl fluoride, polyvinylidene fluoride, tetrafluoroethylene-hexafluoropropylene copolymer, polyamide (PA, Nylon), polyacrylamide, polyacrylonitrile (AN), polyester, polyethylene terephthalate (PET), polybutyrene terephthalate (PBT), polyacetal, polyoxymethylene (POM), polyethylene oxide, polyphenylene oxide (PPO), polyacrylate (=polyacrylic ester), polymethacrylate (=polymethacrylic ester), polyurethane (PUR.AU.EU), polyphenylene sulfide (PPS), polysulfone (PSU), polymethacrylonitrile, or the like.

Thermosetting synthetic resins include phenol-formaldehyde (PF), urea formaldehyde (UF), melamine-formaldehyde (MF), unsaturated polyester (UP), polydiallyl phthalate (PDAP, DAP), aniline-formaldehyde, epoly (EP), furan, xylene-formaldehyde, sulfonamide-formaldehyde, silicone (SI), polyurethane foam, formaldehyde resin, ketone resin, or the like.

The synthetic resin products made of the matrix of the present invention may be applied to a variety of personal ornaments such as necklaces, bracelets, rings or the like, as well as utensil goods such as tablewares.

The products made of the matrix of the present invention can be prepared, in case of the preparation of plastics, as plastic film (industrial use, agricultural use), plastic lump, plastic upper board, plastic bar, pipe and profile, plastic leather, plastic conveyor belt, vinyl wall paper, recycled plastic raw material(powder phase), other plastic primary shaped products, and can be applied, in case of preparation of plastic foamed molded products, for foamed polystyrene (styrofoam etc.), and industrial foamed molded products (including soft and hard products).

For the reinforced plastic molded products, plastics including plastic machinery parts(adding durable, special reinforcing material), and other reinforced plastic molded products can be produced, and for industrial plastic shaping products, plastic electric and electronic machine parts, plastic autocar parts, plastic-made cabinet for home appliances (cabinet for T.V., audio or sewing machine), plastic furniture and other plastic industrial machine parts(pure plastics) can also be produced.

Also household plastic products such as plastic table and kitchen wares(tableware, dish, cup, knife, spoon and so forth), plastic hygiene and cosmetic articles(washbowl, bathtub, soap case, waste basket and so on), plastic button, plastic accessories and other household plastic molded products can be prepared, and plastic molded package vessels such as plastic box(fish box etc.), plastic bottle or similar vessels, and other plastic package vessels can be produced.

Namely, molded products made of the synthetic resin matrix of the present invention can be prepared as various products according to the classification based on the synthetic resin raw material as follows.

PE: bottle, tube, wire coat, food package, film and pipe

PS: doll, kitchen articles, tableware, insulating materials, material for packing, office supplies and parts for related industries such as autocar, electrics and electronics PP: container, pipe, film, artificial leather and parts for autocar AS: kitchen ware, telephone parts and pipe PVC: pipe, film, bottle, doll, disk, food container and wire coat Acryl: optical lens, autocar supplies and protecting plate for T.V.

PA: bearing, hoses and film

PC: electric parts

Fluororesin: gasket and coatings for frying pan

Polyester: various springs(elastic plate), usage for metal insert and gear bearing PF: telephone parts, electric goods, cup and car handle UF: button, lighting apparatus, clock, container, tableware and radio case MF: bathtub, button, safety hat and tableware Unsaturated Polyester: airplane parts, fuel tank, pipe, car body, helmet and fishing rod EP: autocar parts, electric parts and medical supplies PDAP: electric parts, terminal board and micro-switch board PUR: wire coat and rubber SI: tape, releasing agent and defoaming agent Furan: laminated plate and material for electric insulation Xylene: laminated plate molded goods Aniline: goods for electric insulation and laminated plate In addition, ABS, a high-quality resin which is positioned between common resin and engineering plastic, can produce exterior finishing material for electric and electronic goods, and autocar parts as well as telephone, radio, toys, dolls, and in agricultural field, protection for chicken stall against chilling, relieving agent for grain against vermin damage, vinyl house and pot for tree planting, in fishery field, container, artificial seaweeds and fishing implements(rope, fishing net, floating element), in food field, vessel and package for food, in medical field, blood vessel, the gullet, the urethra, the ureter and articulation used in inside of the body, and teeth, eyes, nose, ear and skin used in outside of the body, as well as syringe and diaper, in pharmaceutical field, granules with coating and tablets, in acoustic field, soundproofing agent and anti-vibration agent, in optical field, spectacle lens, contact lens, safety glasses, sun glasses and parts thereof, in textile field, nonwoven, carpet and rain coat in paper field, PE processed paper and plastic foam paper(ps paper), in office supplies field, equipment such as desk and chair, writing materials such as ball pen, in household goods field, tablewares such as kitchen board, dish washing stand and dish, table supplies, and goods for baby such as doll, toy and milk bottle, as well as basket, vegetable box and bathroom goods, in sports field, boat, sports car, skate, tennis racket and golf gloves, in machine field, axial arm, brake shoe, or the like in flight field, wings(main, rear, assist), fuselage, window, bulletin board and safety glass, in shipping field, ship, porthole frame, porthole and door for cabin, in autocar and vehicle field, safety glass, bumper, adiabatic material for car body and foamed cushion for sheet, in communication field, telephone, switchboard and terminal box for telephone, in electronic field, organic semiconductor, in electric field, electric fan, washing machine, television, radio, refrigerator and hairdressing tools, in building field, interior- and exterior-finishing materials such as ceiling material, wall material, floor material, tile and board for verandah, in engineering works field, admixture(for example, cement), water-protecting plate and tree-planting in desert, in information and printing fields, synthetic resin type, synthetic resin reprint, synthetic resin electric mold and magnetic tape, in atomic energy field, reaction vessel and various coating materials, in space development field, storage tank for liquid hydrogen and liquid oxygen, and in packing container field, plastic container and alternate plastic film.

The molding process for synthetic resin matrix according to the present invention is a well-known method and follows the methods described in the Table below.

TABLE

| Raw materials for the synthetic resin | Injection molding (thermoplastic resin) Press molding (thermosetting resin) Transfer molding (thermosetting resin) Extrusion molding (thermoplastic resin) Blow molding (thermoplastic resin) Vacuum molding (thermoplastic resin) Compression molding (thermoplastic resin film) Foaming molding (thermoplastic resin) Deposit molding (thermoplastic resin) |
|---|---|

The particle size of the nephrite jade powder used in the preparation of the matrix according to the present invention may be selected as considering the shape and use of the molded article. Generally, nephrite jade powder having the particle size of 100–350 mesh is preferably used. If the shape of the molded article is complicated, or increased ductility is required, for example, in case that the article has a small thickness, more fine particles (about 250–350 mesh) are preferable used, while 100–500 mesh powder may be added in order to prepare a general molded article. If the particle size is higher than the range, it is disadvantageous because the surface roughness of the article becomes larger, while the particle size is lower than the range, difficulties occurs in the pulverization.

The amount of nephrite jade added to the raw materials (resin) of the articles is desirably 5–15%. If the amount is less than 5%, the effect of nephrite jade cannot be expected. The larger the amount, the better effect of nephrite jade occurs. However, if the amount is beyond the range, the properties of the raw material resin (in particular, ductility) is lowered to make the article brittle, molding flowability is lowered, and increase the cost of the product owing to the high price of nephrite jade.

The nephrite jade powder used in the present invention may be originated from the remaining stone of nephrite jade after making the products of personal ornaments, vessels or sculpture, in order to lower the production cost to enhance the economics. By using the matrix, a variety of goods for practical use which have the inherent properties of nephrite jade may be obtained with far lower cost than that of the products made of nephrite jade itself. Besides, the products made of the matrix of the present invention have enhanced mechanical or thermal properties (such as heat resistance, tensile strength, compression strength, etc) as compared to those not containing nephrite jade.

The nephrite jade powder used in the present invention is cryptocrystalline tremolite of $\sigma^{18}O$, having a composition shown in the following Table 1.

TABLE 1

Results of Semi-quantitative Analysis of the Nephrite Jade Powder used in the Present Invention (%)

| Silicon | 34 | Tin | 0.024 |
|---|---|---|---|
| Magnesium | 10 | Beryllium | 0.00072 |
| Calcium | 4.9 | Silver | 0.0013 |
| Iron | 0.23 | Titanium | 0.0038 |
| Aluminum | 0.16 | Nickel | 0.0028 |

TABLE 1-continued

Results of Semi-quantitative Analysis of the Nephrite
Jade Powder used in the Present Invention (%)

| Copper | 0.17 | Chromium | 0.0030 |
|---|---|---|---|
| Cobalt | 0.046 | Other element | 0 |
| Manganese | 0.14 | | |

DESCRIPTION OF THE PREFERRED EMBODIMENT

The preparation of synthetic resin products which contain nephrite jade powder according to the present invention, and effects demonstrated in the products are described in more detail with reference to the following Examples.

EXAMPLE 1

Nephrite jade powder (10 parts by weight) pulverized to 150 mesh of particle size was admixed with 90 parts by weight of polyethylene, a kind of thermoplastic resin. The admixture was injected into an injection mold through the hopper, and heated to 100°–130° C. to press into the mold with increasing ductility.

The molded articles of various type (a variety of vessels such as tablewares, personal ornaments such as necklaces, bracelets or rings, and other ornaments) were obtained after cooling the mold.

EXAMPLE 2

Nephrite jade powder (10 parts by weight) pulverized to 150 mesh of particle size was admixed with 90 parts by weight of polyethylene. The admixture was injected into an injection mold, and heated to 35° to 45° C. to press into the mold with increasing ductility by using a ram.

The molded articles of various type (tablewares, teacups, ornaments, necklaces, bracelets, rings or earrings) were obtained.

EXAMPLE 3

Nephrite jade powder (10 parts by weight) pulverized to 300 mesh of particle size was admixed with 90 parts by weight of polyethylene. The admixture was injected into an injection mold, and heated to 35° to 45° C. to press into the mold with increasing ductility by using a ram.

The molded articles of various type such as tablewares, teacups, ornaments, necklaces, bracelets, rings or earrings were obtained.

The synthetic resin products prepared as described above have high heat resistance and impact resistance. Besides, if they are used as tablewares the freshness of food can be maintained for a longer time by virtue of far infrared ray generated from nephrite jade. In addition, in case of keeping the ornaments of the present invention on human body, certain therapeutic effects appear in the body (see Experimental Examples below).

Experimental Example 1

This is to examine whether lead, heavy metals or other toxic materials exist in the nephrite powder used in the preparation of matrix of the present invention (FDA registration No.: 2022038, Bio-Science Research Institute, Inc.).

TABLE 2

(Test for Lead Content)

| Sample | Nephrite jade Powder |
|---|---|
| Experimental method | Atomic Absorption Analysis |
| Working No. | IW 091394-1 |
| Results | Not detected |

TABLE 3

(Test for Heavy Metals)

| Sample | Nephrite jade Powder |
|---|---|
| Experimental method | USP 23 |
| Working No. | IW 080894-4 |
| Results | Not detected |

TABLE 4

(Test for Dissociation of Inorganic materials)

| Sample | Nephrite jade Powder |
|---|---|
| Experimental method | The sample (about 100 g) was extracted with 1 liter of water in an autoclave, and the extract was analysed. |
| Working No. | IW 080894-4 |
| Results | Listed below |

| Analysed Material | Result (ppm) | Detection limit (ppm) |
|---|---|---|
| As | ND | 0.05 |
| Ba | ND | 0.20 |
| Cd | 0.006 | 0.005 |
| Cl | ND | 1 |
| Cr | ND | 0.01 |
| Cu | ND | 0.05 |
| Fe | ND | 0.10 |
| Pb | ND | 0.05 |
| Mn | ND | 0.02 |
| Hg | ND | 0.0005 |
| $NO_3$ | ND | 0.1 |
| Se | ND | 0.05 |
| Ag | ND | 0.01 |
| $SO_4$ | 1.85 | 1 |
| Zn | ND | 0.01 |

ND = Not detected, or the concentration lower than the detection limit

As shown in the above experimental results, the nephrite jade powder used in the preparation of the matrix of the present invention does not contain any material having toxicity to human body, such as lead, heavy metals or other materials. Thus, the articles prepared in the present invention are proved to be safe if they are used as tablewares.

Experimental Example 2

The test cup (prepared according to Example 2) and control cup (made of polyethylene) were filled with homogenized Grade A milk, and allowed to stand for 48 hours at ambient temperature. Then, the milk was subjected to analysis. The results are shown in Table 5 below.

TABLE 5

| Tests | Control Cup | Test Cup |
|---|---|---|
| Coliform Bacteria | Absent/ml | Absent/ml |
| Lactobacillus | 45000 cfu/ml | 37000 cfu/ml |
| Yeast & Mold Count | 310 cfu/ml | 280 cfu/ml |
| Standard Plate Count | over $3 \times 10^6$ cfu/ml | over $3 \times 10^6$ cfu/ml |

Conclusion : The number of microorganisms which are harmful to human body was reduced.

Experimental Example 3

Figure 2A:
FIG. 2 is a SEM photograph of silk not treated with nephrite jade-water.
Figure 2B:
Figure 3A:
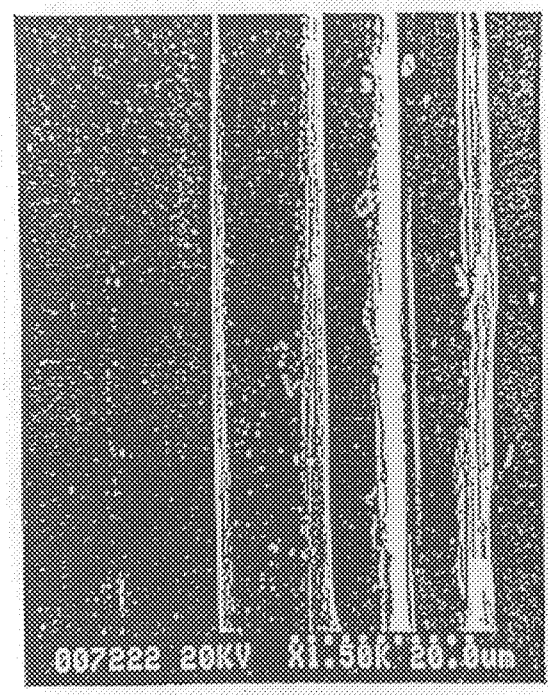
FIG. 3 is a SEM photograph of silk treated with nephrite jade-water which contains a matrix according to the present invention.
Figure 3B:
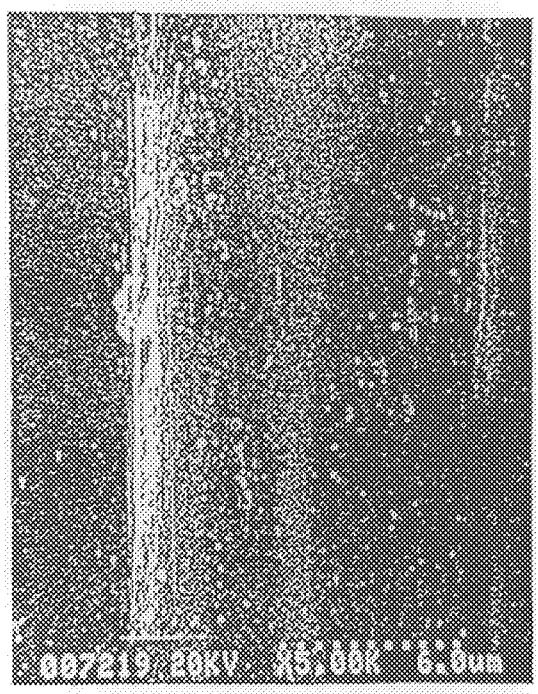

Piped water was purified through a filter filled with the matrix prepared in Example 1, and the effect of the obtained jade-treated water on the growth of silkworm and the quality of the produced silk (see FIGS. 1–3).

Materials and Methods
1. Species of silkworm: white gem silkworm
2. Period of growth: November to December
3. Method for growth: constant temperature and constant humidity, fed with mulberry leaves during all instars
4. No. of silkworms: control group 150 (×2 repetition)
    treated group 130 (×2 repetition)
5. Treatment;
    control group: Mulberry leaves sprayed with distilled water are fed.
    treated group: Mulberry leaves sprayed with jade-treated water are fed.
    time to treat the silkworms: starting from 2nd instar

TABLE A

Rearing results performed with the jade powder water treatment

|  | replication | No. of larvae examined | larval period of the 5th instar day.hrs | total larval period day.hrs | pupation percentage % | index |
| --- | --- | --- | --- | --- | --- | --- |
| Control | 1 | 150 | 7.07 | 23.07 | 91.3 | |
| | 2 | 150 | 7.07 | 23.07 | 76.6 | |
| | mean | 150 | 7.07 | 23.07 | 84.0 | 100 |
| Treatment | 1 | 130 | 7.15 | 23.15 | 74.1 | |
| | 2 | 130 | 7.15 | 23.15 | 68.2 | |
| | mean | 130 | 7.15 | 23.15 | 71.2 | 85 |

|  | replication | cocoon yields (kg/10,000) | index | single cocoon weight g | index | cocoon shell weight cg | index | cocoon shell percentage % | index |
| --- | --- | --- | --- | --- | --- | --- | --- | --- | --- |
| Control | 1 | 17.9 | | 2.08 | | 43.0 | | 20.7 | z |
| | 2 | 15.0 | | 1.96 | | 39.0 | | 19.9 | |
| | mean | 16.5 | 100 | 2.02 | 100 | 41.0 | 100 | 20.3 | 100 |
| Treatment | 1 | 16.2 | | 2.14 | | 44.0 | | 20.6 | |
| | 2 | 14.6 | | 2.14 | | 45.0 | | 21.0 | |
| | mean | 15.4 | 93 | 2.14 | 106 | 44.5 | 109 | 20.8 | 102 |

TABLE B

The performances of cocoon reeling with jade powder water treatment

| | cocoon filament length m | cocoon filament weight cg | silk size d | nonbreaking length of bave m | nonbroken filament weight cg | reel-ability % |
| --- | --- | --- | --- | --- | --- | --- |
| control | 1,222 | 33.7 | 2.48 | 8.47 | 23.4 | 69 |
| treatment | 1,283 | 36.3 | 2.55 | 1,005 | 28.5 | 78 |

| | percentage of raw silk % | neatness point | tenacity g/d | elongation % | weight of raw silk kg |
| --- | --- | --- | --- | --- | --- |
| control | 16.68 | 95 | 3.80 | 17.4 | 2.75 |
| treatment | 16.96 | 96 | 3.93 | 18.0 | 2.61 |

TABLE C

The change of larval weight with jade treatment

| | weight of newly exuviated larva from the 3rd molting | weight of newly exuviated larva from the 4th molting | weight of the 3rd day of the 5th instar | matured larvae |
| --- | --- | --- | --- | --- |
| control | 0.46 | 1.85 | 20.80 | 47.4 |
| treatment | 0.47 | 1.94 | 23.03 | 52.2 |

TABLE D

Decreasing effects of blood glucose content by jade solution

| | amount of blood glucose | | decreasing effects of blood glucose | |
| --- | --- | --- | --- | --- |
| | injected | injected with | | |
| silkworm extracts | with[†] maltose (A) mg/100 ml | silkworm extracts (B) mg/100 ml | amount (C = A − B) mg/100 ml | efficiency % |
| treated with water | 64.0 ± 1.87 | 27.7 ± 1.70 | 36.3 | 56.7 |
| treated with jade solution | 69.6 ± 1.62 | 20.7 ± 1.62 | 48.9 | 70.3 |

[†]: Before injection of silkworm extracts

Results
1. The larva weight of the jade-treated group was higher than that of the control group in every instar. In particular, in case of mature larva, the weight of the jade-treated group was higher by 0.48 g per larva than that of the control group.

2. The single cocoon weight of the jade-treated group was 2.14 g, which was higher by about 6% than that of the control group. In addition, the cocoon shell weight of the jade-treated group was 44.5 cg, which was higher by about 9% than that of the control group. The cocoon shell percentage of the jade-treated group was higher by 2% as expressed by index than that of the control group.

3. The reeling performance of the jade-treated group was generally better than that of the control group. In particular, the jade-treated group was excellent in view of the cocoon filament length, cocoon filament weight and reelability (higher by 9% than that of the control group).

4. No substantial difference between the surface structure of the control group and the jade-treated group was revealed.

5. The decreasing effects of blood glucose content of the jade-treated group was 70.3%, which was higher by 24% than that of the control group.

Experimental Example 4

The experiment was performed to investigate the effect of jade container (bowl) made of the matrix of the present invention on the freshness of pork when pork had been stored in the bowl. The experiment was performed by Korea Food Research Institute. Details are described below:

Pork was stored either in a jade bowl or in a plain bowl (control) for 0, 4, 7, 14 or 21 days at 0° C. or 4° C. One hundred gram (100 g) of pork cut from ham part was kept in each container, while the drip loss, meat color, pH, volatile basic nitrogen(VBN: protein-denaturation) and lipid oxidation (TBA) were measured. The results are shown in Table 6 and FIGS. 13–17.

Figure 15A:
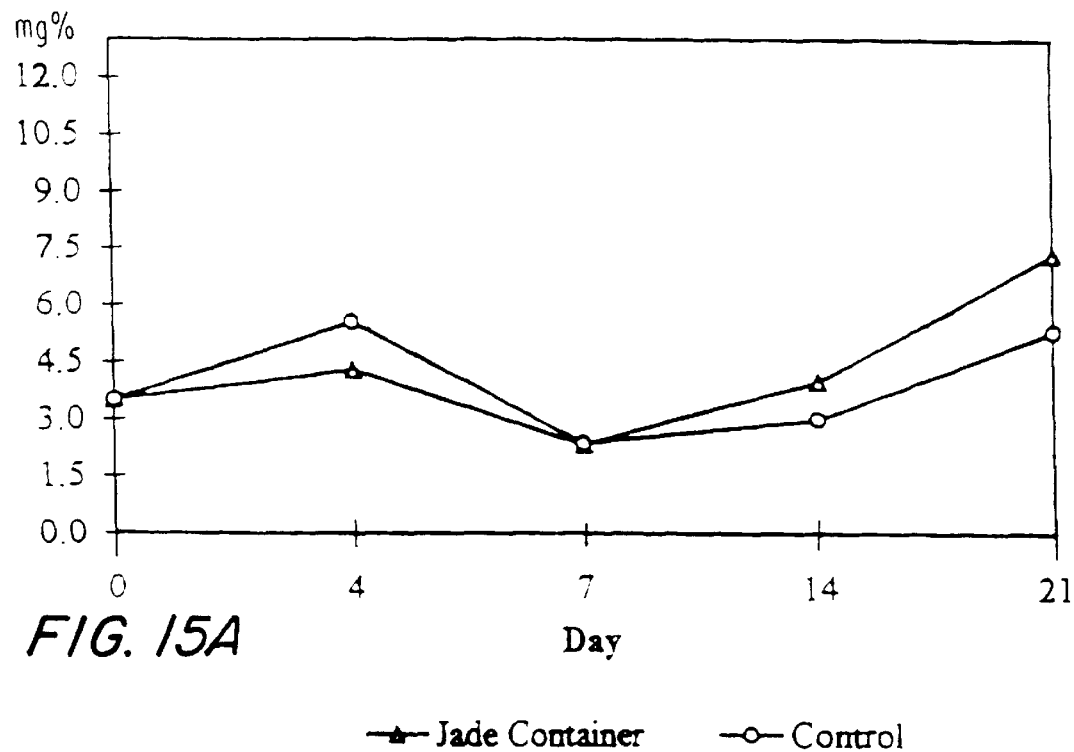
FIG. 15 shows the effect of jade container on VBN content when pork was stored at 0° C. or 4° C. for 21 days.
Figure 15B:
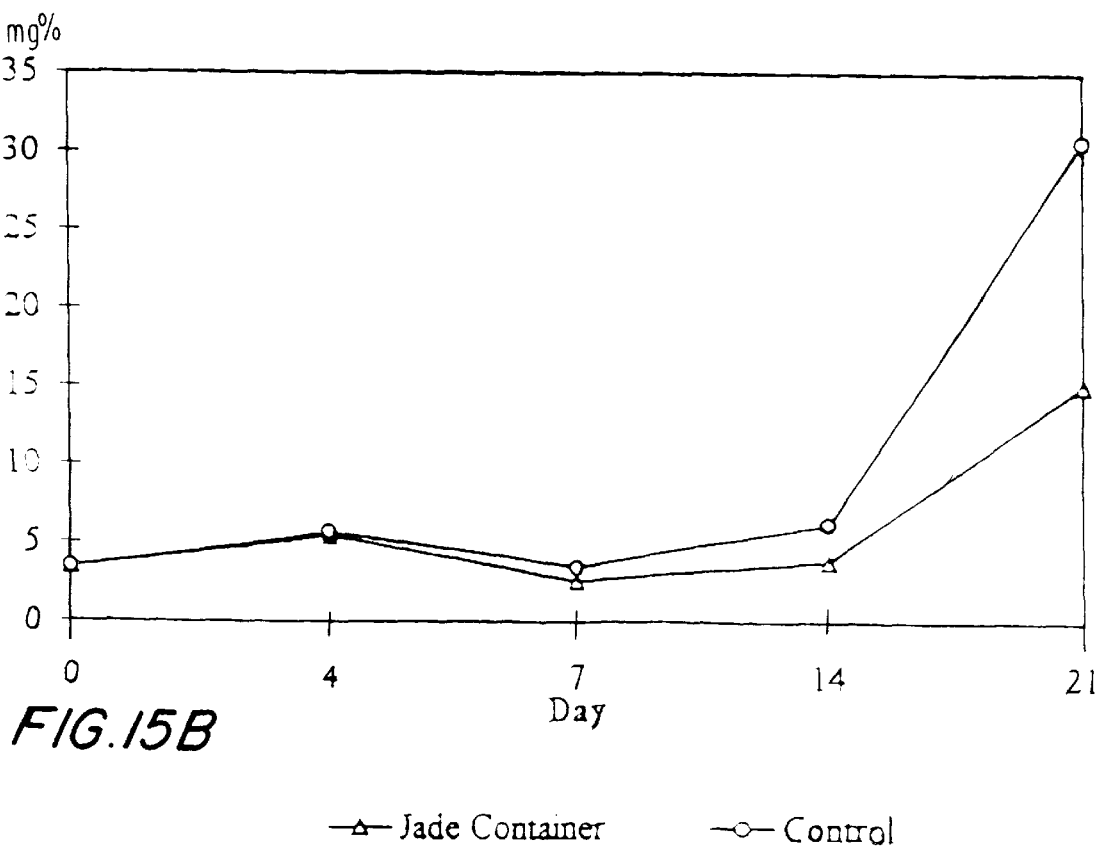

FIG. 15 shows the effect of jade container on VBN content when pork was stored at 0° C. or 4° C. for 21 days.

Figure 16A:
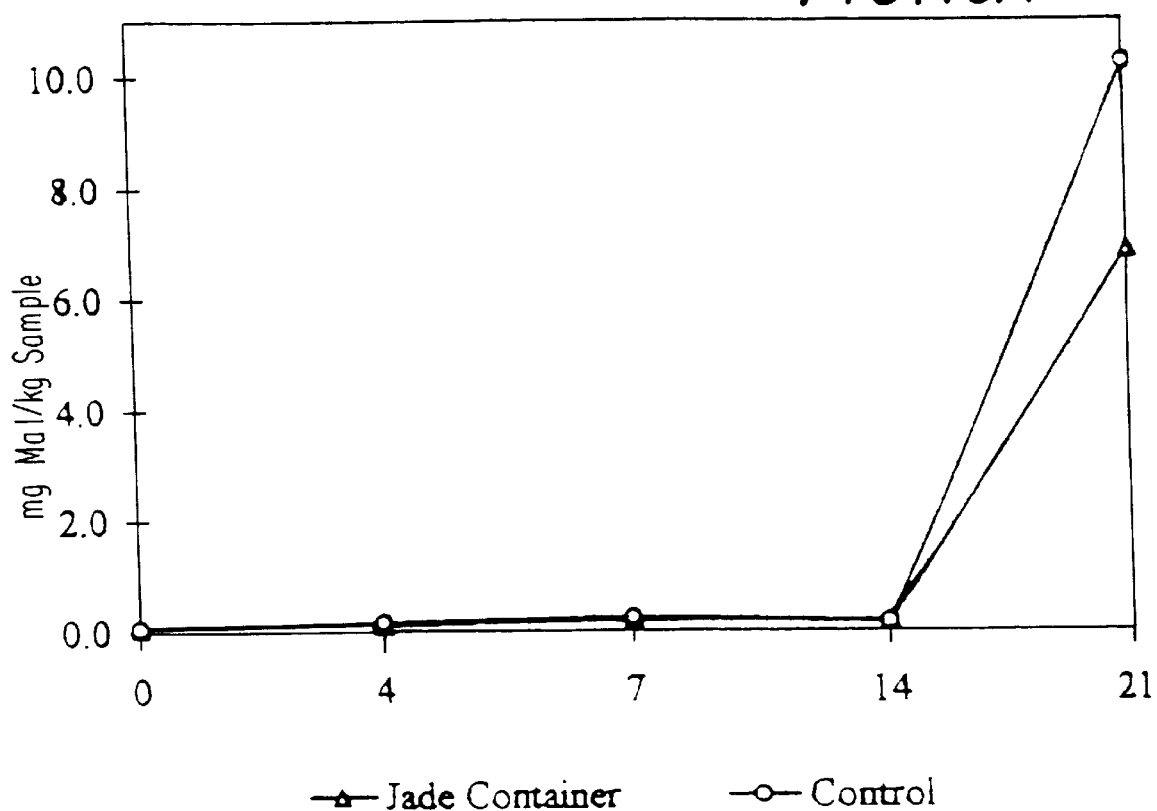
FIG. 16 shows the effect of jade container on TBA value when pork was stored at 0° C. or 4° C. for 21 days.
Figure 16B:
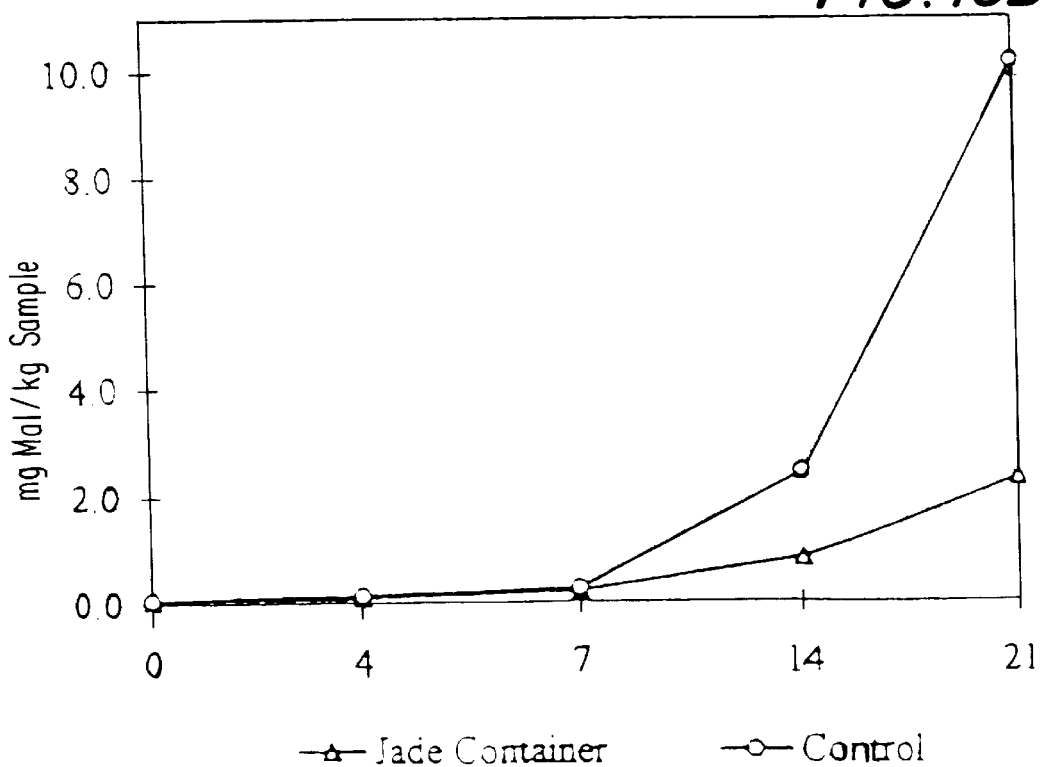

FIG. 16 shows the effect of jade container on TBA value when pork was stored at 0° C. or 4° C. for 21 days.

Figure 17A:
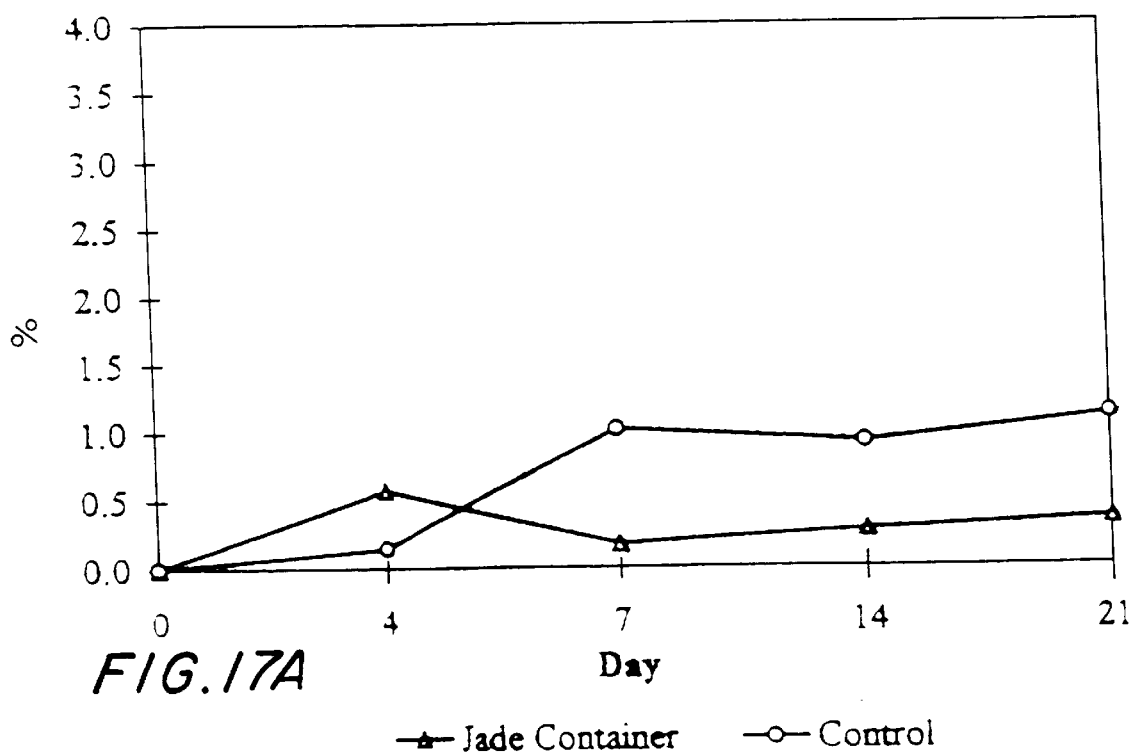
FIG. 17 shows the effect of jade container on drip loss (%) when pork was stored at 0° C. or 4° C. for 21 days.
Figure 17B:
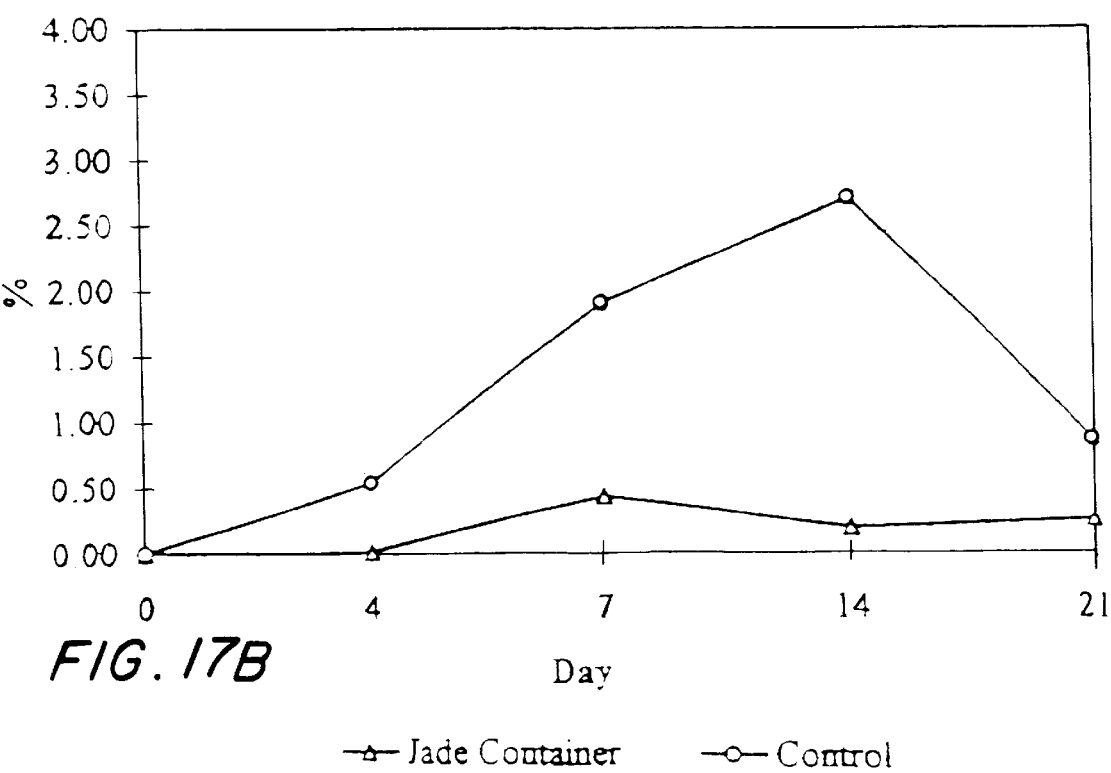

FIG. 17 shows the effect of jade container on drip loss (%) when pork was stored at 0° C. or 4° C. for 21 days.

As can be seen from the results, drip loss was much less in pork stored in jade bowl and tended to be considerably reduced as time passed by, regardless of the storage temperature. As an important indicator of postmortem change of muscles, pH normally lowers down immediately after slaughter and then remains as high as 6.5–6.8. In the present experiment, type of the container did not seem to affect pH change (though pH at 4° C. was higher than that at 0° C.) and VBN value (which indicate the degree of protein denaturation) of pork directly. However, TBA value (which indicates the degree of lipid oxidation) was kept lower in pork stored in jade bowl regardless of the storage temperature. Meat color was measured by color difference meter due to absorption and reflection of meat color pigment. $\Delta E$ value was lower in control (plain bowl group) than in jade bowl group at 0° C. and no consistent tendency was observed in pork stored at 4° C. though $\Delta E$ value at 0° C. was lower than that of 4° C. This might be resulted from higher metmyoglobin formation due to more dehydration caused by high temperature.

From the experiment, if containers made of jade or packing materials (such as polyvinyl film) coated with jade powder are used in storing food, sanitary and quality might be maintained in the distribution of corruptible food, thereby lengthen the shelf life and enhance the safety.

TABLE 6

Effects of Jade Container on the Parameters Affecting Pork Quality

| Temp (°C.) | | 0 | | 4 | |
| --- | --- | --- | --- | --- | --- |
| Container | | Control | Jade | Control | Jade |
| Day 0 | Color ($\Delta E$) | | 53.70 ± 4.34 | | |
| | pH | | 5.83 ± 0.04 | | |
| | VBN | | 3.50 ± 0.43 | | |
| | TBA | | 0.063 ± 0.013 | | |
| Day 4 | Color ($\Delta E$) | 55.80 ± 0.01 | 49.30 ± 0.11 | 54.90 ± 0.08 | 56.50 ± 0.07 |
| | pH | 5.46 ± 0.04 | 5.42 ± 0.00 | 5.59 ± 0.01 | 5.69 ± 0.01 |
| | VBN | 5.56 ± 0.20 | 4.29 ± 0.20 | 5.65 ± 0.39 | 5.42 ± 1.41 |
| | TBA | 0.153 ± 0.00 | 0.104 ± 0.032 | 0.122 ± 0.006 | 0.099 ± 0.025 |
| | Drip loss (%) | 0.14 | 0.57 | 0.54 | 0.01 |
| Day 7 | Color ($\Delta E$) | 55.50 ± 0.47 | 52.60 ± 0.75 | 52.80 ± 0.06 | 52.90 ± 0.05 |
| | pH | 5.77 ± 0.03 | 5.84 ± 0.01 | 5.56 ± 0.01 | 5.65 ± 0.01 |
| | VBN | 2.36 ± 0.00 | 2.32 ± 0.00 | 3.48 ± 0.45 | 2.59 ± 0.22 |
| | TBA | 0.234 ± 0.013 | 0.203 ± 0.006 | 0.239 ± 0.006 | 0.203 ± 0.019 |
| | Drip loss (%) | 1.02 | 0.17 | 1.90 | 0.43 |
| Day 14 | Color ($\Delta E$) | 51.70 ± 0.10 | 53.80 ± 0.13 | 62.80 ± 0.00 | 56.70 ± 0.04 |
| | pH | 5.50 ± 0.01 | 5.67 ± 0.03 | 6.71 ± 0.00 | 5.91 ± 0.02 |
| | VBN | 3.00 ± 0.39 | 3.98 ± 0.18 | 6.17 ± 0.87 | 3.85 ± 0.53 |
| | TBA | 0.162 ± 0.013 | 0.176 ± 0.019 | 2.406 ± 0.191 | 0.811 ± 0.089 |
| | Drip loss (%) | 0.92 | 0.27 | 2.70 | 0.19 |
| Day 21 | Color ($\Delta E$) | 52.40 ± 0.06 | 59.20 ± 0.13 | 58.20 ± 0.13 | 66.30 ± 0.33 |
| | pH | 6.41 ± 0.01 | 6.07 ± 0.00 | 7.24 ± 0.00 | 6.69 ± 0.01 |
| | VBN | 5.32 ± 0.36 | 7.35 ± 0.42 | 30.67 ± 3.31 | 15.08 ± 0.98 |
| | TBA | 10.220 ± 0.230 | 6.852 ± 0.274 | 10.15 ± 0.198 | 2.298 ± 0.102 |
| | Drip loss (%) | 1.11 | 0.35 | 0.85 | 0.25 |

VBN: mg %
TBA: mg Mal/kg of meat

Figure 13A:
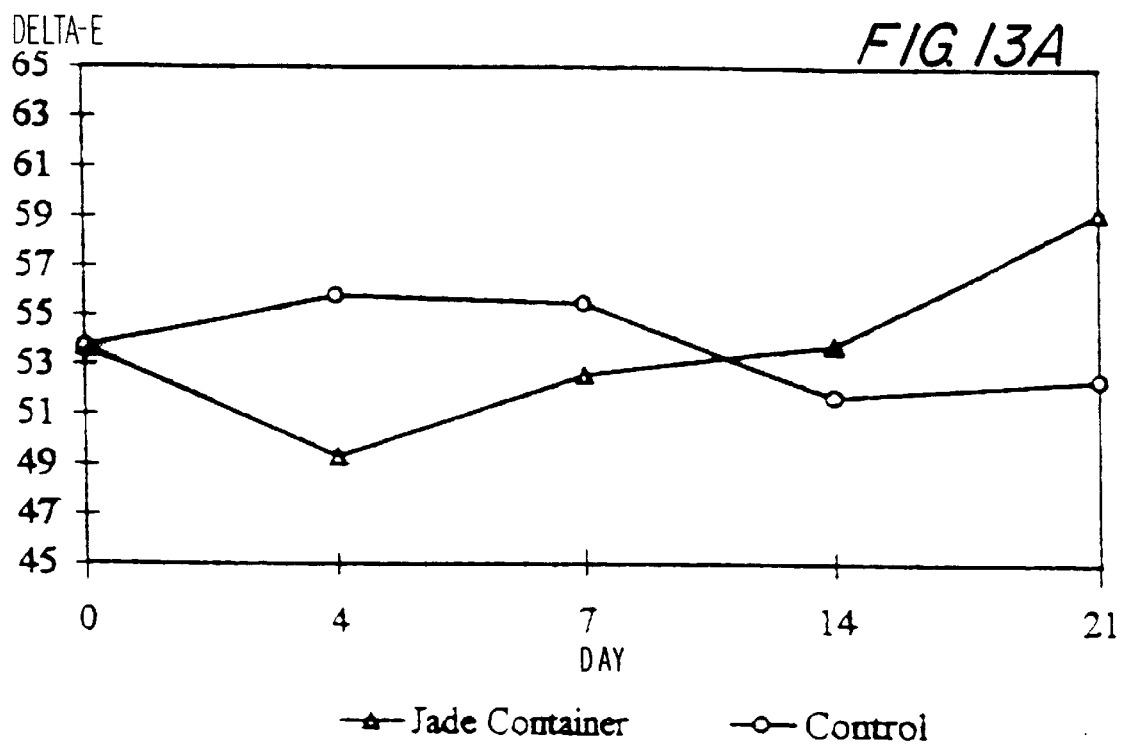
FIG. 13 shows the effect of jade container on meat color($\Delta E$) when pork was stored at 0° C. or 4° C. for 21 days.
Figure 13B:
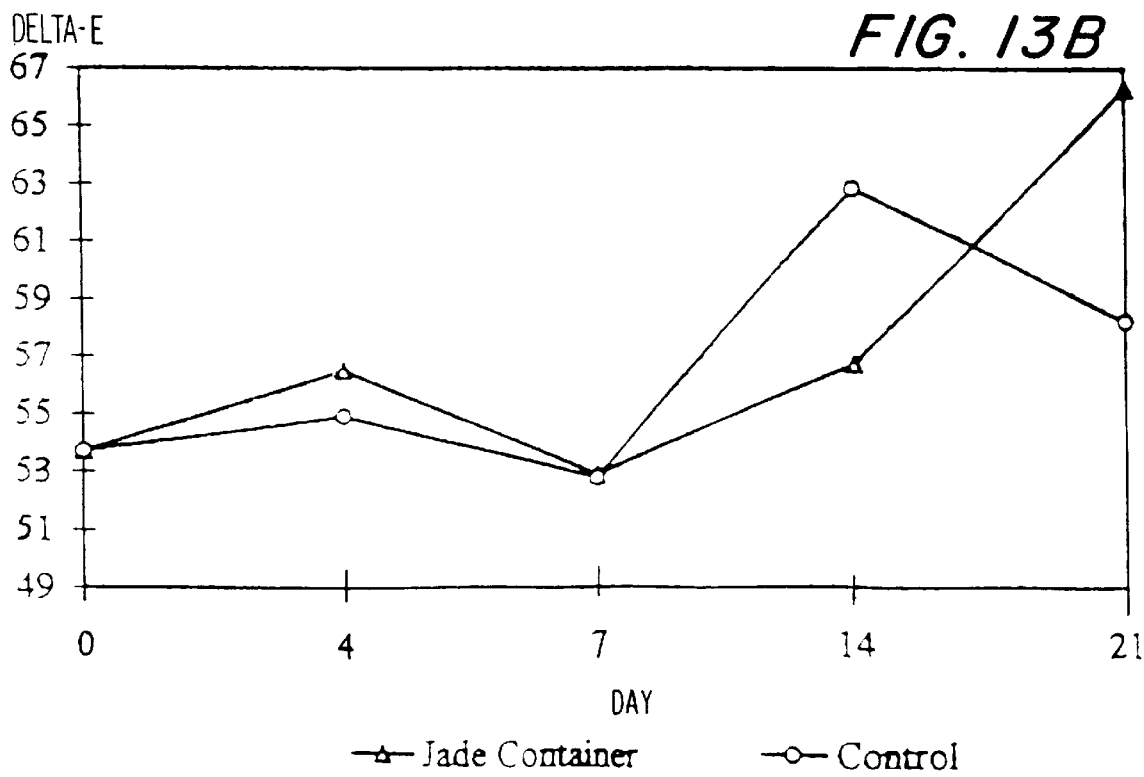

FIG. 13 shows the effect of jade container on meat color($\Delta E$) when pork was stored at 0° C. or 4° C. for 21 days.

Figure 14A:
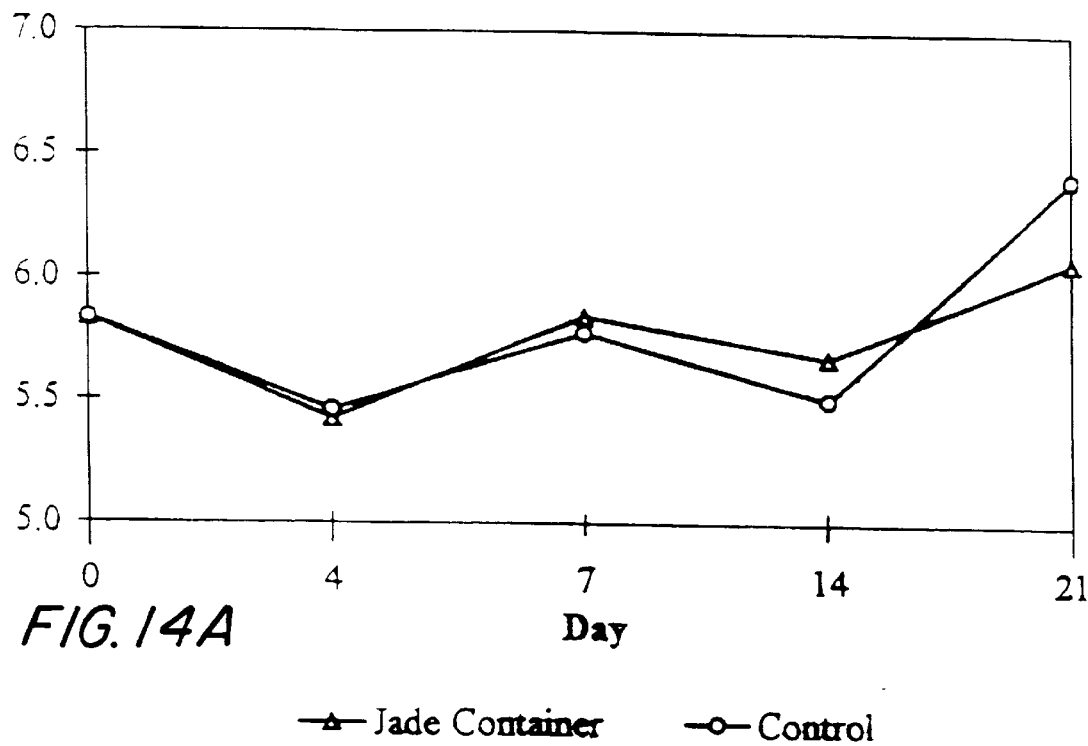
FIG. 14 shows the effect of jade container on meat pH when pork was stored at 0° C. or 4° C. for 21 days.
Figure 14B:
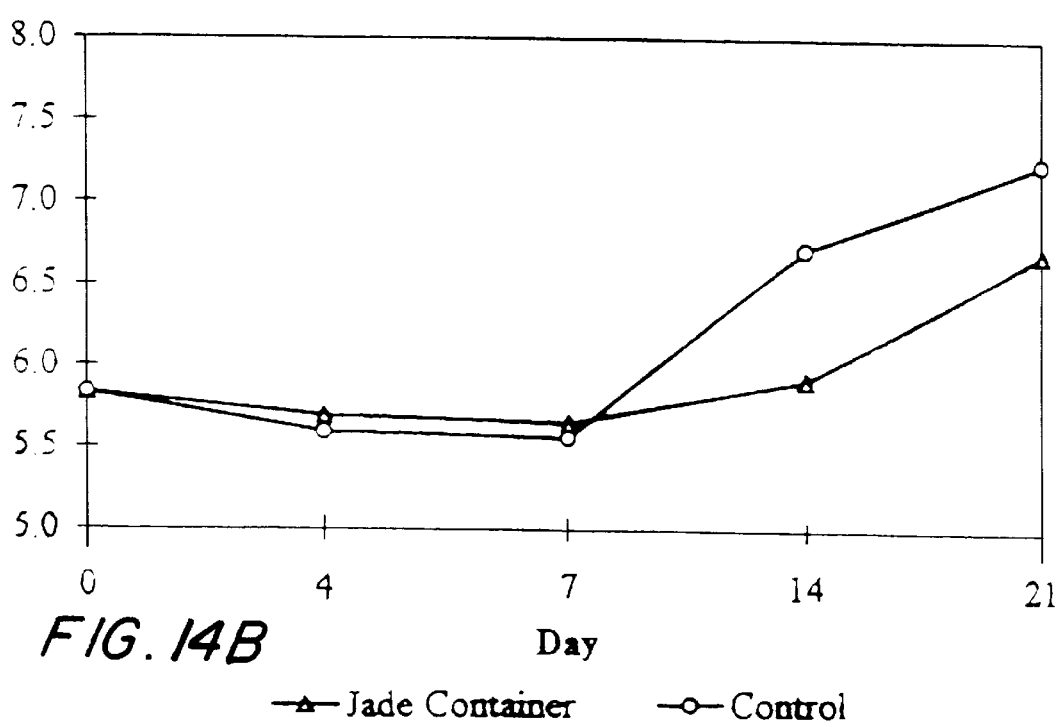

FIG. 14 shows the effect of jade container on meat pH when pork was stored at 0° C. or 4° C. for 21 days.

Experimental Example 5

The IR study of nephrite jade powder used in the preparation of the matrix according to the present invention was performed.

| Sample | Jade Powder |
|---|---|
| Appearance | White powder |
| Experimental method | Perkin Elmer 137 |
| Working No. | IW 080894-4 |
| Results | Described below |

IR condition:

Phase: Tetrahydrofuran liquefied thin film
Results: The IR spectrum appears to conform to polycarbonate resin patterns, and to emit the electromagnetic wave having 6–52$\mu$ of wavelength.

Experimental Example 6

The COD (Chemical Oxygen Demand) and BOD (Biochemical Oxygen Demand) of the jade powder used in the matrix of the present invention were tested.

| Sample | Jade Powder | |
|---|---|---|
| Appearance | White powder | |
| Experimental method | Standard methods | |
| Results | Described below | |
| | water (control) | jade-treated |
| BOD for 5 days | 224 mg/l | 223 mg/l |
| COD | 115 mg/l | 110 mg/l |

Experimental Example 7

The effect of nephrite jade powder contained in the matrix of the present invention on the test animals (rabbits) was examined in this Experimental Example.

TABLE 7

| (Primary Eye Irritation Study) | |
|---|---|
| Sample | Jade Powder |
| Appearance | Milk-white powder |
| Experimental method | Described below |
| Results | Described below |

Methods: Federal Register, Vol.43. No.163 -Aug. 22, 1978, p.37359

Procedure: Extract (0.1 ml) was placed on the everted lower lid of one eye; the upper and lower lids were then gently held together for 1 second before releasing. The other eye, remaining untreated, served as a control. The treated eyes of six rabbits remained unwashed and those of three rabbits were flushed for one minute with lukewarm water immediately after treatment. The eyes were pre-examined using fluorescein procedures prior to treatment with sample and only those showing no corneal injury were used in the test. Readings of ocular lesions were taken at 24 hours, 48 hours, 72 hours, 7 days and 14 days after treatment.

Results:

TABLE 8

| Rabbits | Time | Corneal Opacity | Area of Cornea | Iris Values | Conj. R. | Conj. Ch. | Conj. Dis. |
|---|---|---|---|---|---|---|---|
| #1 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #2 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #3 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #4 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #5 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #6 | 24 H | 0 | 0 | 0 | 0 | 0 | 0 |
| Unwashed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #7 | 24 H | 0 | 0 | 0 | 0 | 0 | 0 |
| Washed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #8 | 24 H | 0 | 0 | 0 | 0 | 0 | 0 |
| Washed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |
| #9 | 24 H | 0 | 0 | 0 | 0 | 0 | 0 |
| Washed | 48 H | 0 | 0 | 0 | 0 | 0 | 0 |
| | 72 H | 0 | 0 | 0 | 0 | 0 | 0 |
| | 7 D | 0 | 0 | 0 | 0 | 0 | 0 |
| Scores | | Cornea (0) | | Iris (0) | Conjunctivae (0) | | |

I. Cornea
   (A) Opacity—Degree of Density (Area taken for reading)
      Normal—0
      Scattered of diffuse area—details of iris clearly visible—1
      Easily discernible translucent areas, details of iris slightly obscured—2
      Opalescent areas, no details of iris visible, size of pupil barely discernible—3
      Opaque, iris invisible—4
   (B) Area of Cornea Involved
      Normal—0
      One quarter (or less) but not zero—1
      Greater than one quarter, less than one half—2
      Greater than one half, less than three quarters—3
      Greater than three quarters up to whole area—4
         Score equals A×B×5, Total Maximum=80
II. Iris
   (A) Values
      Normal—0
      Folds above normal, congestion, swelling, circumcorneal injection (any size one or all of these or combination of any thereof), iris still reacting to light (sluggish reaction is positive)—1

No reaction to light, hemorrhage, gross destruction (any one or all of these)—2

Score A×5, Total Possible Maximum=10

III. Conjunctivae (A) Redness (Refers to palpebral conjunctivae only)
Normal—0
Vessels definitely injected above normal—1
More diffuse, deeper crimson red, individual vessels not easily discernible—2
Diffuse beefy red—3

(B) Chemosis
No swelling—0
Any swelling above normal (includes nictitation membrane)—1
Obvious swelling with partial eversion of the lids—2
Swelling with lids about half closed—3
Swelling with lids about half closed to completely closed—4

(C) Discharge
Normal—0
Any amount different from normal (does not Include small amount observed in inner canthus of normal animals)—1
Discharge with moistening of the lids and hairs just adjacent to the lids—2
Considerable area around the eye—3
Score (A+B+C)×2. Total Maximum=20

Conclusion: The sample is adjudged to be free from eye irritants and, thus, suitable for cosmetic use in eye-care products.

TABLE 9

(Primary Dermal Irritation Study)

| Sample | Jade Powder |
|---|---|
| Appearance | White powder |
| Experimental method | Described below |
| Results | Described below |

Methods: Federal Register, Vol.43. No.163

CTFA (The Cosmetic, Toiletry and Fragrance Association, Washington, D.C.) Technical Guidelines Procedure: The procedure utilized a patch test technique on the abraded and intact skin of the albino rabbit. The hair was clipped from the back and flanks. Two areas of the back, spaced approximately 10 cm apart, were designated for the position of the patches. One area was abraded by making 4 minor epidermal incisions (2 perpendicular to the other in a "tic-tac-toe pattern) in the area of the patch. The 1 inch square patches of surgical gauze were secured in place using thin rubber bands and adhesive tape. The sample was introduced under the patch 0.5 ml (g) each site. The entire trunk of the animal was then wrapped with rubberized cloth for the 24-hour period of exposure. The animals were restrained during the exposure period. After removal of the patches, resulting reactions at each site were evaluated on the basis of the weighted scores described below.

Evaluation of Skin Reactions

Erythema and Eschar Formation
No erythema—0
Very slight erythema (barely perceptible)—1
Well defined erythema—2
Moderate to severe erythema—3
Severe erythema (beet redness) to slight eschar formation (injuries in depth)—4

Edema Formation
No edema—0
Very slight edema (barely perceptible)—1
Slight edema (edges of area well defined by raising)—2
Moderate edema (raised approximately 1 mm)—3

Results:

|  | 24 Hours | | | | 72 Hours | | | |
|---|---|---|---|---|---|---|---|---|
|  | Intact | | Abraded | | Intact | | Abraded | |
| Rabbits | ER | ED | ER | ED | ER | ED | ER | ED |
| #1 | 0 | 0 | 0 | 0 | 0 | 0 | 0 | 0 |
| #2 | 0 | 0 | 0 | 0 | 0 | 0 | 0 | 0 |
| #3 | 0 | 0 | 0 | 0 | 0 | 0 | 0 | 0 |
| #4 | 0 | 0 | 0 | 0 | 0 | 0 | 0 | 0 |
| #5 | 0 | 0 | 0 | 0 | 0 | 0 | 0 | 0 |
| #6 | 0 | 0 | 0 | 0 | 0 | 0 | 0 | 0 |

Conclusion: The sample is adjudged to be free from skin irritants and, thus, suitable for cosmetic use in skin-care products.

TABLE 10

Acute oral toxicity (0.5 g/100 g weight) test

| Sample | Nephrite jade powder |
|---|---|
| Appearance | White powder |
| Experimental Method | Described below |
| Results | Described below |

| Mouse | Sex | Initial weight(g) | Dose (ml) | Later weight(g) | Toxicity |
|---|---|---|---|---|---|
| 1 | F | 207 | 1.0 | 219 | None |
| 2 | F | 211 | 1.1 | 226 | None |
| 3 | F | 215 | 1.1 | 225 | None |
| 4 | F | 208 | 1.0 | 217 | None |
| 5 | F | 200 | 1.0 | 213 | None |
| 6 | M | 227 | 1.1 | 235 | None |
| 7 | M | 216 | 1.1 | 224 | None |
| 8 | M | 205 | 1.0 | 218 | None |
| 9 | M | 210 | 1.1 | 224 | None |
| 10 | M | 212 | 1.1 | 221 | None |

Preparation of sample : The sample was extracted by boiling with sterile distilled water. The extract was administered through a cannula with an amount of 0.5 g per 100 g weight of the animal.

Conclusion : The sample conforms to the standard stating that it should have no oral toxicity.

Experimental Example 8

The experiment is to examine the effects of a jade mug which might change the taste attributes of beverage (commercial instant coffee) when the beverage is served in a jade container. The experiment was performed by Department of Food & Nutrition of Chung-Ang University and Korea Food Research Institute. The details are described below:

1> Object of the experiment

To examine the change in taste, aroma, aftertaste and/or color of coffee when it is served in a jade mug or a plain mug (control).

2> Test method : Paired Preference Test
to test preference of one sample over the other sample
test attributes: taste, aroma, aftertaste, color
3> Sensory Panels
20–25 students majored in food & nutrition at Chung-Ang University in Korea (who are experienced with panel test and have knowledge on the test method)
4> Test Period
March to June, 1996
once a week
Totally 10 times were performed.
5> Test container and type of beverage
A jade mug vs. a plain mug: both having same appearance
Beverage: instant coffee (Taster's Choice)
6> Sample preparation
1 tea spoon of coffee was mixed to ½ cup of hot water.
7> Statistics: T-test ($p \leq 0.05$)
Results
1. Taste: Coffee contained in jade mug imparted much less bitter taste ($p \leq 0.05$).
2. Color & Aftertaste: Jade mug tended to give better color and aftertaste, but statistically non-significant.
3. Aroma: Plain mug gave better coffee aroma than jade mug.
* FIG. 4 shows the effect of jade mug on sensory attributes of coffee.

Conclusion

Jade mug seems to make the taste of coffee mild (which is proved to be statistically significant). Aftertaste and color of the coffee contained in jade mug was similar to or better than that contained in plain mug (not statistically significant). Aroma of coffee contained in plain mug was better than that in jade mug (not statistically significant).

Experimental Example 9

The effect of nephrite jade powder contained in the matrix of the present invention was examined in this Experimental Example to confirm its influences on a living organism. To examine whether such powder actually influences the activities of the plant cells, experiment for the effects of nephrite jade powder on the proliferation of Digitalis plant cells has been performed at Bio-information System Engineering Laboratory in Inha University by applicant's request.

The results of the bioengineering experiment of nephrite jade will be described as follows.

As human body consists 70% of water, there may be many relationships between the change of water and influences on human body. Therefore, the effects of nephrite jade on hard water and then, proliferation of Digitalis plant cells are examined.

I. The change of hard water

Procedure 1

Fifty milliliters of hard water(hardness:100 ppm) artificially made is transferred to 4 flasks respectively and nephrite jade is placed in two of these flasks for 10 mins.

The titration using EDTA(factor: 2.9412) is performed to determine the change of hardness. The buffer solution(pH 10) 1 ml and EBT as an indicator are used.

The change of hardness is determined by amount of EDTA used till the moment that the color of hard water is changed by EDTA. At this time, color may be restored to original color as time passes but in present experiment, determination is made at the changing point.

Result 1

|  | hard water(control) | After treated with nephrite jade |
|---|---|---|
| amount of EDTA used in titration(ml) | 1.70 | 1.25 |
| hardness(ppm) | 100 | 73.53 |
|  | — | decreasing 26.47% of hardness |

Procedure 2

Hard water(hardness: 100 ppm) 200 ml prepared in accordance with Procedure 1 is transferred to a flask and nephrite jade is dipped thereinto.

After 30 mins, water filled in the flask is divided into 3 flasks and the change of hardness is determined. In this procedure, EDTA is dropped until there is no more color change after the color of hard water is changed by EDTA so as to perform a more precise experiment and hardness at that point is measured.

Result 2

|  | hard water before treatment with nephrite jade (control) | | | hard water after treatment with nephrite jade | | |
|---|---|---|---|---|---|---|
|  | #1 | #2 | #3 | #1 | #2 | #3 |
| hardness (ppm) | 100 | 100 | 100 | 89.62 | 91.19 | 89.62 |
| average hardness (ppm) |  | 100 |  |  | 90.14 |  |
|  |  | — |  |  | decreasing 9.9% of hardness |  |

Procedure 3

This procedure is performed with ordinary piped water. The piped water charged in a container is transferred to 6 flasks and the nephrite jade is placed on the bottom of 3 flasks among above flasks. The hardness is determined after 5 mins.

|  | piped water (control) | | | piped water treated with nephrite jade | | |
|---|---|---|---|---|---|---|
|  | 1 | 2 | 3 | 4 | 5 | 6 |
| hardness (ppm) | 97.48 | 97.48 | 97.48 | 91.19 | 91.19 | 91.19 |
| average hardness (ppm) |  | 97.48 |  |  | 91.19 |  |
|  |  | — |  |  | decreasing 6.5% of hardness |  |

Figure 5:
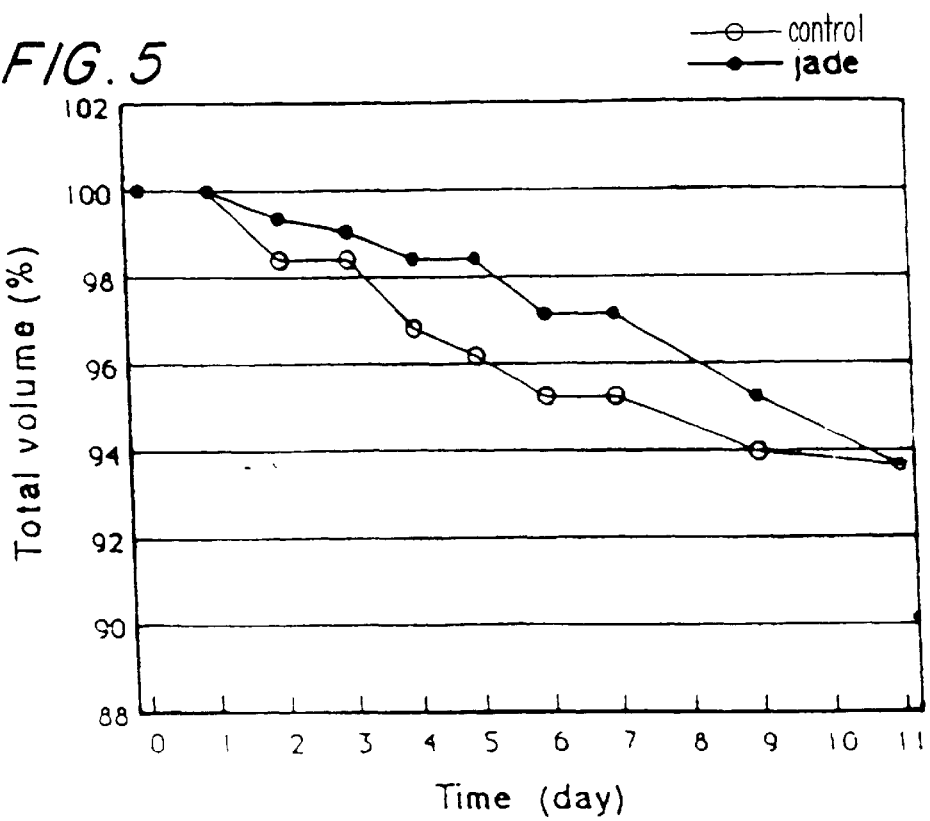
FIG. 5 shows the volume change of the whole culture medium for culturing Digitalis Ianata (Experimental Example 9).
Figure 6:
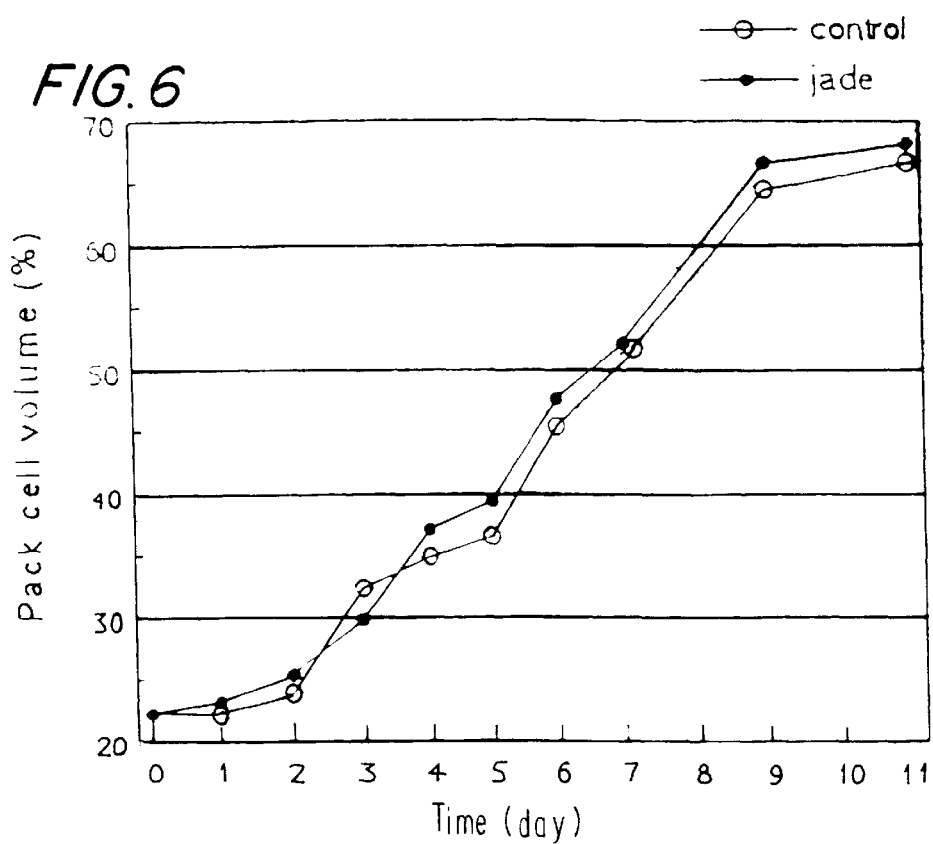
FIG. 6 shows the change of the cell volume (Experimental Example 9) of Digitalis Ianata.

II. The effect of nephrite jade on proliferation of Digitalis lanata suspended plant cell suspension ① The effect of nephrite jade on cell growth of Digitalis lanata in growth medium The change of medium liquor's total volume of the cells proliferating in growth medium is observed for 11 days and the result is shown in FIG. 5. Because the depletion of ingredients in medium and evaporating of medium occur in proportion to increasing of the cells growing with time, overall change in volume of medium liquor reflects these figures. Specially, the humidity and temperature of air have close relationships with evaporating of medium and these figures also influence the rate of cell growth. As shown in FIG. 5, total volume of medium liquor in case that nephrite jade is used reduces little by little compared to that in control that nephrite jade is not used. When nephrite jade is used, the rate of cell growth opposed to evaporating of medium and depletion of nutrients is faster than that of the control and by this reason, rapid decreasing of medium depleted can be somewhat offset. As shown in FIG. 6, which measures the volume change of packed cells only, from 4 days till 11 days after inoculation cell volume in case of using nephrite jade continuously is observed to increase more than that in control case of using no nephrite jade. Hence, when nephrite jade is used, the rate of cell growth is more rapid than that wherein nephrite jade is not used. These results are understood that reduction of total volume of medium liquor due to depletion of nutrients and medium evaporation is offset by rapid cell growth rate in this experiment using nephrite jade and this results in that decreasing rate of total volume of medium liquor will be retarded compared to control. In addition, the result comparing exact volume of proliferated cells shows the increasing tendency of cells' volume gradually after 4 days and is also understood to support above-mentioned conclusions.

The full weight and dry weight of the cells are measured as a most general index for determining the proliferating state of cells. The growth curve of every cells is generally represented in sigmoidal curve and this sigmoidal curve will be divided into 4 phases: the lag phase wherein there is no cell proliferation and no mass increasing, and which is an adapting time for medium; the exponential phase which shows a steep slope because mass is increased due to rapid proliferation rate after passing the lag phase; the stationary phase wherein cell growth reaches at maximum to what extent and proliferation is being held and there is no mass increasing; and, the dead phase wherein overall cells' volume or mass is reduced because cells are dead by rupture due to depletion of nutrients, secretion of toxic components and saturation state of cell density.

Figure 7:
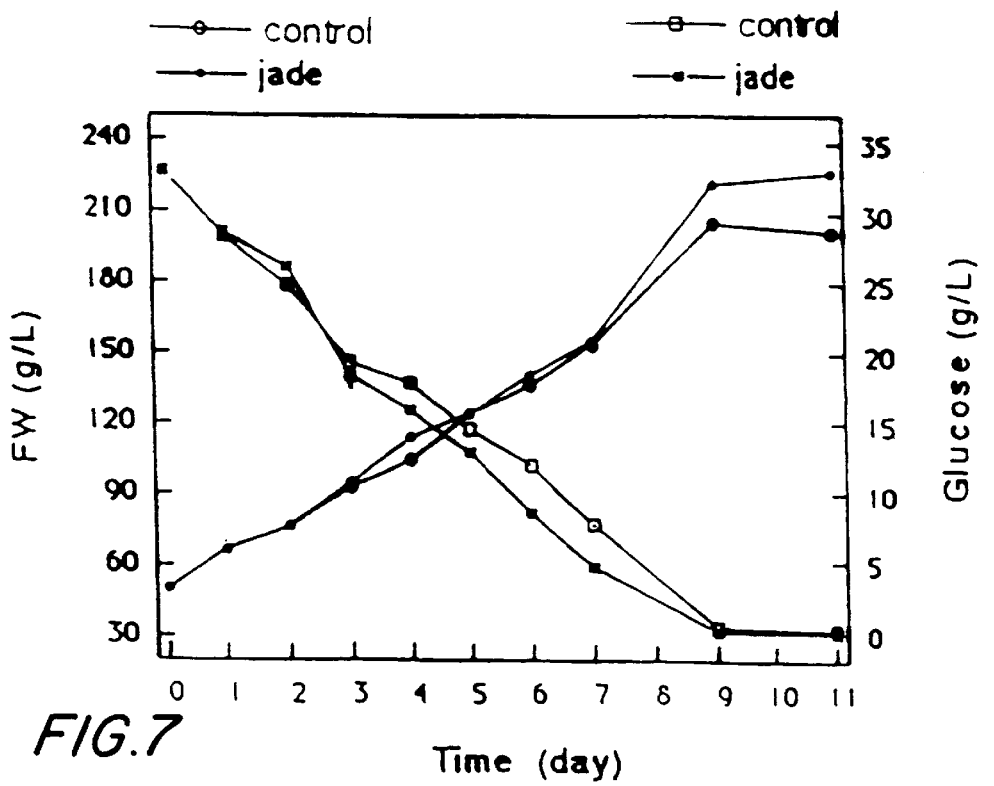
FIG. 7 shows the change of the weight of the biological organisms of the cell (Experimental Example 9).
Figure 8:
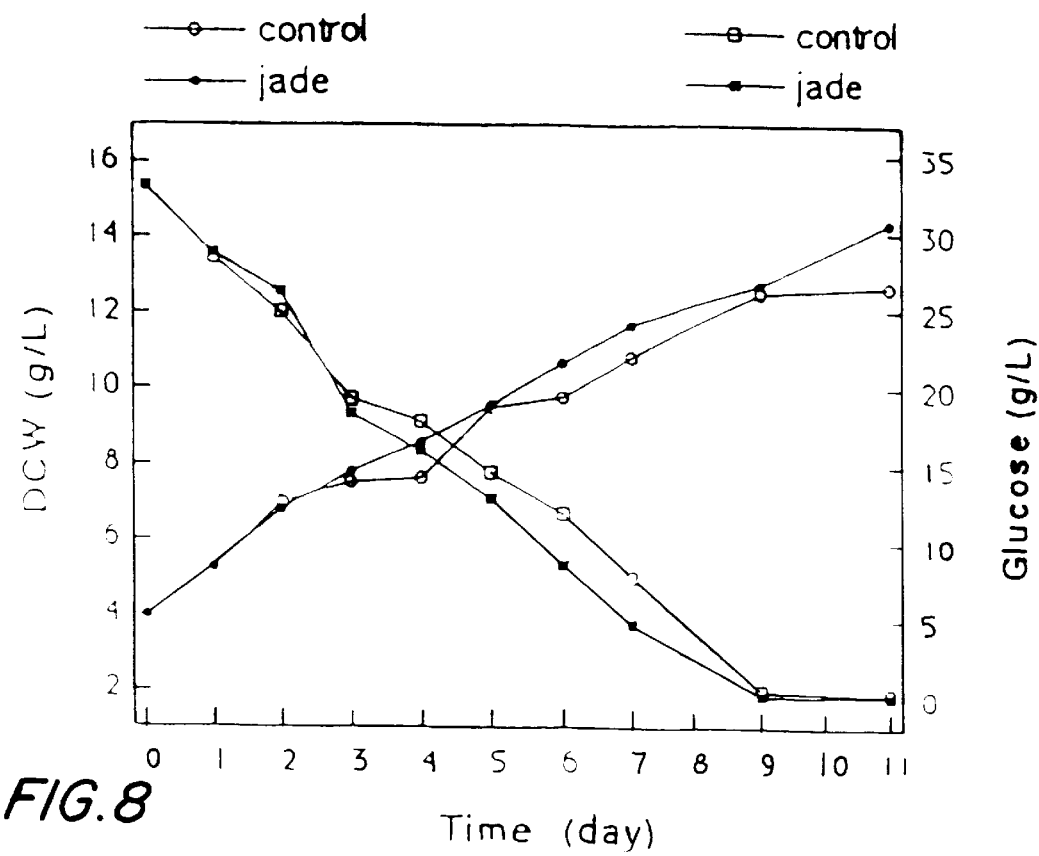
FIG. 8 shows the change of the dry weight of the cells (Experimental Example 9).

FIGS. 7 and 8 are results of measuring full weight and dry weight of cells. FIG. 7 follows above-mentioned 4 phases growth curve. The group using nephrite jade shows a little rapid proliferation rate than the control group using no nephrite jade after 7 days later, and proliferation in the former tends to continue until 10 days later while that in the latter is stopped and full weight of cells reduces. When the concentration change of glucose, a nutrient acting as a main metabolic substrate in medium, is compared, it is notable that cell growth in medium according to the present invention is continued at the point that the concentration of glucose approaches to zero by virtue of depletion of such nutrient, while, generally in the control medium (nephrite jade is not used), the proliferation is stopped and the rate of cell growth is decreased at the point that nutrient is being exhausted . This suggests that nephrite jade may have influences on cell growth. Such result is also shown in FIG. 8 which is a graph of measuring the dry weight of cells. In FIG. 8, the cell growth in medium of the present invention (nephrite jade is used) represents more rapid proliferation rate than that in the control medium (nephrite jade is not used) after 3 days later and the same appearance as in FIG. 7 appears since 9 days later.

Therefore, the cells cultured in growth medium being close to nephrite jade shows good effect on cell growth compared to the control. When Digitalis Ianata plant cells which have about 10 days' growth limit are cultured using nephrite jade, above cells maintain the stable state wherein cell necrosis does not happen without exchange with a new medium until 10 days later, and rather show the cell proliferation. By such reasons, the method according to the present invention may be applied for optimization of cell growth and concentration in favorable manner as a process for producing the useful material.

② The effect of nephrite jade on pH change of the medium

Figure 9:
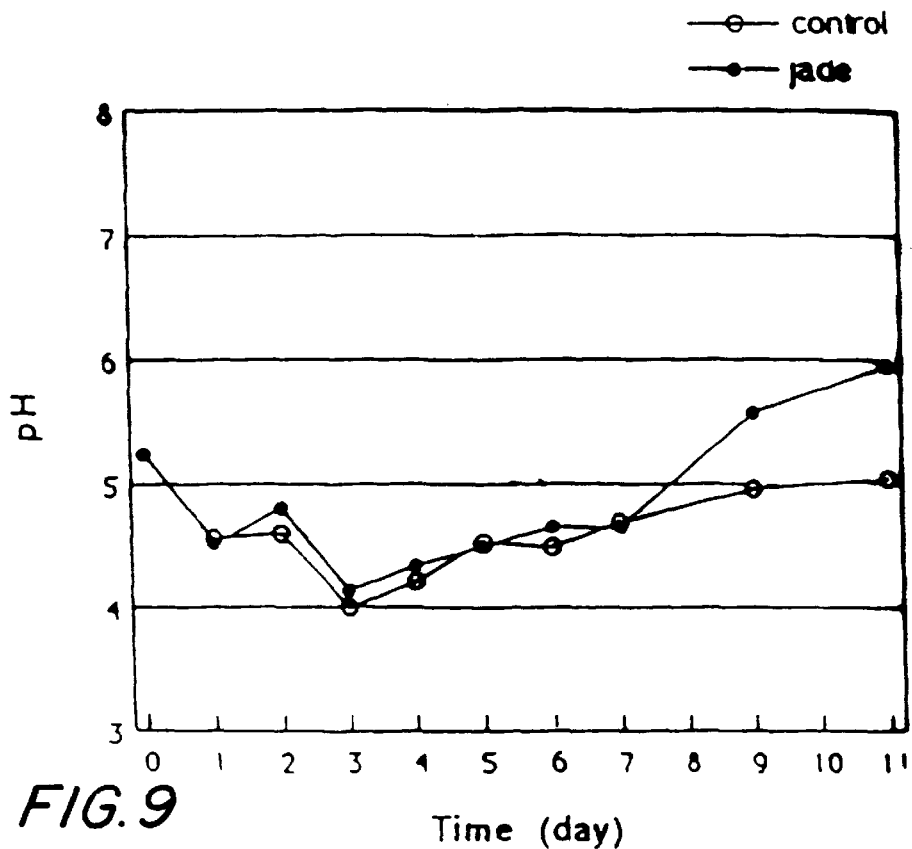
FIG. 9 shows the change of pH in the culture medium for Digitalis Ianata (Experimental Example 9).
Figure 10:
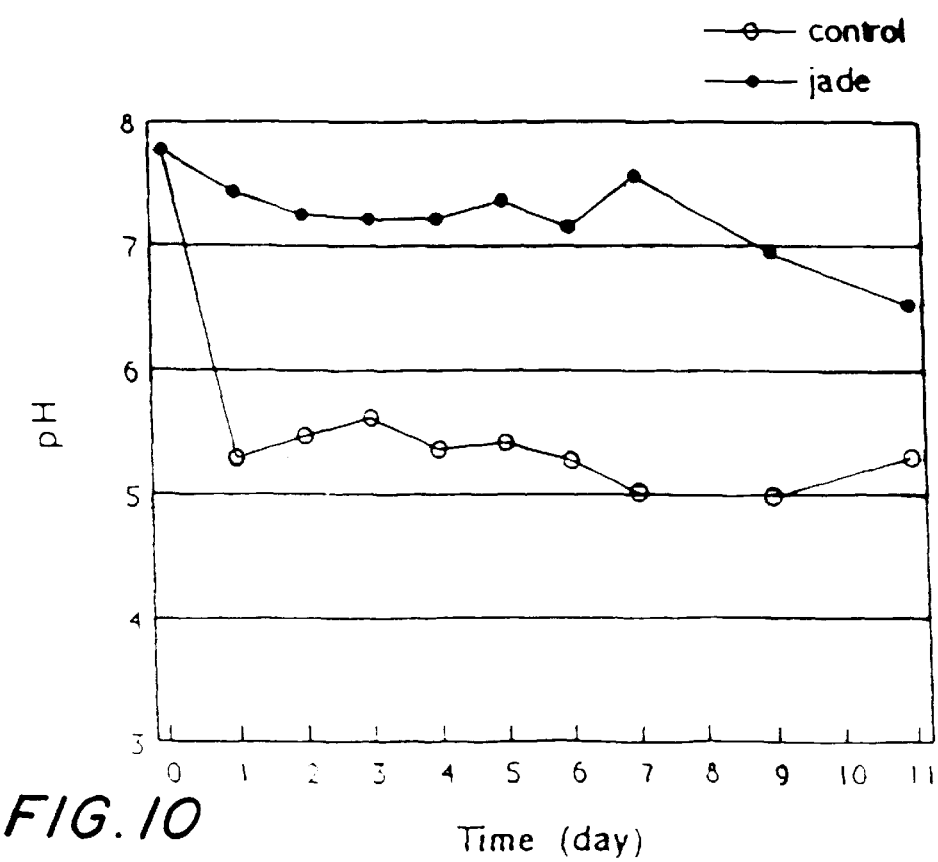
FIG. 10 shows the change of pH of the culture medium after adding nephrite jade powder (Experimental Example 9).
Figure 11:
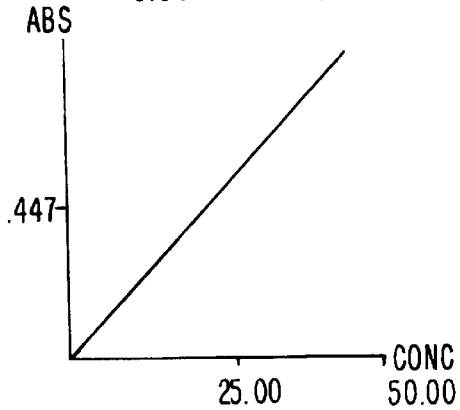
FIG. 11 shows the condition of the analytical instrument (Experimental Example 9).

FIG. 9 is a graph of measuring pH change in the medium using the nephrite jade and in the control medium using no nephrite jade. In control, pH tendency in the medium applied in typical plant cells also appears and pH decreases gradually with time and then, keeps to some level. However, when nephrite jade is used, pH tendency is similar to that of the control till 7 days later but pH increases little by little hereafter. Such phenomenon is obviously appeared in FIG. 10 which is a graph of measuring pH change in medium wherein nephrite jade powder is directly added. While pH value decreases continuously in the control medium wherein nephrite jade is not added, pH value of the medium wherein nephrite jade is added tends to maintain at some degree. It is supposed that ion reaction due to mineral ingredients contained in the nephrite jade may act as a cause for above result.

③ The result of analysis experiment for water quality to nephrite jade

Table A and B represent the condition of analysis apparatus and analysis result, and from these Tables, the data is arranged to each sample and the results are shown in Tables C to F. In Table C, each analysis item is measured to (sample 1) 48 hours later after the addition of a lump of 20 g nephrite jade and there is no change in each analysis item and hence, there is no influence due to nephrite jade. In Table D, each analysis item is measured to (sample 2) 48 hours later after a lump of 20 g nephrite jade is placed out of solution, and also there is no change in each analysis item. In Table F, there is no change in each analysis item of this analysis experiment wherein a lump of 20 g nephrite jade is placed out of solution (sample 4). However, in case of sample 3, data measuring each analysis item against sample passed 48 hours after addition of 20 g nephrite jade powder into the solution are shown in Table E. As shown in Table E, there are many changes and these changes are as follows.

The amounts of Cr, Pb, Ni and Co which are harmful to human body are changed greatly after 48 hours. The amount of Cr before the addition of nephrite jade powder, i. e. before the reaction, is 45.30 mg and it becomes to zero 48 hours later after the addition of nephrite jade. And also Pb is completely removed from 13.76 mg to zero. The amount of Ni decreases from 51.8 mg to 1.733 mg and the amount of Co also decreases from 52.69 mg to 11. 94 mg.

The amount of Magnesium, one of essential ingredients for human body, increases from 48.36 mg to 55.74 mg and this results from the binding of Mg with component of nephrite jade itself but there is no change in hardness.

The hydrogen ion concentration of the distilled water appears as acidic of pH 3.5 but changes to neutral of pH 6.8, and the conductivity decreases rapidly. The adsorptive power is about 3–4 mmol.q (equivalent) per 1 g and it is a high value in physical sense.

TABLE C

Result of analysis before and after the reaction
(nephrite jade mass (20 g) in solution)

| Item | Before reaction | After reaction (48 hr) | Amount of change |
|---|---|---|---|
| pH | 3.5 | 3.82 | – |
| Ni | 51.8 mg | 51.75 mg | – |
| Co | 52.69 mg | 52.54 mg | – |
| Cr | 45.30 mg | 43.88 mg | – |
| Mg | 48.36 mg | 48.59 mg | – |
| Pb | 13.76 mg | 13.90 mg | – |

TABLE D

Result of analysis before and after the reaction
(nephrite jade mass (20 g) out of the solution)

| Item | Before reaction | After reaction (48 hr) | Amount of change |
|---|---|---|---|
| pH | 3.5 | 3.65 | – |
| Ni | 51.8 mg | 48.92 mg | – |
| Co | 52.69 mg | 49.83 mg | – |
| Cr | 45.30 mg | 41.23 mg | – |
| Mg | 48.36 mg | 47.97 mg | – |
| Pb | 13.76 mg | 15.1 mg | – |

TABLE E

Result of analysis before and after the reaction
(nephrite jade powder (20 g) in the solution)

| Item | Before reaction | After reaction (48 hr) | Amount of change |
|---|---|---|---|
| pH | 3.5 | 6.8 | +3.3 |
| Ni | 51.8 mg | 1.733 mg | −50.6 mg |
| Co | 52.69 mg | 11.94 mg | −40.75 mg |
| Cr | 45.30 mg | 0 mg | −45.30 mg |
| Mg | 48.36 mg | 55.74 mg | +7.38 mg |
| Pb | 13.76 mg | 0 mg | −13.76 mg |

TABLE F

Result of analysis before and after the reaction
(nephrite jade powder (20 g) out of the solution)

| Item | Before reaction | After reaction (48 hr) | Amount of change |
|---|---|---|---|
| pH | 3.5 | 3.7 | – |
| Ni | 51.8 mg | 51.53 mg | – |
| Co | 52.69 mg | 52.55 mg | – |
| Cr | 45.30 mg | 43.0 mg | – |
| Mg | 48.36 mg | 48.39 mg | – |
| Pb | 13.76 mg | 14.29 mg | – |

As described above, the proliferation of Digitalis Ianata plant suspension cell which have been cultured for a week near nephrite jade was increased by about 30% as compared to the same cell cultured without nephrite jade. The obtained result is very surprising because the result like this has not been occurred at all in the various experiments previously performed to examine the proliferation of Digitalis Ianata plant cell for high concentration culture.

In addition, in the experiment of change of hard water, was found the fact that nephrite jade softened the hard water even without contacting with water.

In particular, in the experiments of elemental analysis for distilled water in which nephrite jade powder has been precipitated, a special results of increasing pH, reducing Ni and Co, removal of heavy metals such as Cr, Pb and increasing of Mg have occurred.

Though the effect of nephrite jade (powder) used in the matrix of the present invention has not yet been clarified theoretically, the effects [such as changing of hard water without contacting water, increasing the proliferation of Digitalis Ianata plant suspension cell by 30%, reducing Ni and Co, and removing heavy metals such as Cr and Pb, which have human toxicity] are surely due to the emission of electromagnetic waves shown in the results of the IR study, Experimental Example 5, and ionic reactions of inorganic components contained in nephrite jade.

The results shown above suggest the possibility of removing heavy metals and softening hard water if a synthetic resin vessel made of the matrix according to the present invention is used in the storage of food or drinking water; and the possibility of promoting the growth of biological organisms if the synthetic resin product made of the matrix is used as a plating dish or a flower pot.

Experimental Example 10

To fifty adults (men and women) having symptoms of headache, insomnia, numb feeling of hands or foots, or indigestion, at least one of the personal ornaments (necklace, earring, ring) prepared according to Example 2 had been taken for 20 days, and the effect of the ornaments was examined by questionnaire. The results are shown in the Table below.

| | No effect | Effective | Considerable effect | Almost perfect cure | Total |
|---|---|---|---|---|---|
| headache | 3 | 6 | 5 | 1 | 15 |
| insomnia | 3 | 7 | 4 | 2 | 16 |
| numb feeling | 1 | 6 | 1 | 2 | 10 |
| indigestion | 1 | 6 | 2 | 0 | 9 |
| Total | 8 (16%) | 25 (50%) | 12 (24%) | 5 (10%) | 50 (100%) |

As can be shown in the above results, the symptoms of headache (80%), insomnia (81%), numb feeling (89%) and indigestion (89%) was alleviated when the personal ornaments made of the matrix containing nephrite jade powder according to the present invention had been attached to the body.

Experimental Example 11

The experiment is to examine the effects of jade powder and jade water on the sterilization by ultraviolet ray. The experiment was performed by department of biology in Hanyang University. The details are described below:

1. Sample collection

Samples (jade powder and jade water) were collected from the jade miners located in Wolgok-ri, Dong-myun, Chuncheon-kun, Kangwon-do.

2. Bacterial strains and growth condition

Strains of *Escherichia. coli* (Gram−), *Bacillus subtilis* (Gram+) and *saccharomyces cerevisiae* (Eucaryote), which are closely related to animal skin, were used as control microorganisms. Nutrient agar (yeast extract 3g, bacto-peptone 5 g, sodium chloride 8 g/D.W 1) was used for strains of *Escherichia. coli* (Gram−) and *Bacillus subtilis* (Gram+). After incubation at 37° C. for 24 hours, the colonies were counted. YPD (yeast extract 3 g, bacto-peptone 10 g, dextrose 30 g/D.W. 11) was used for *Saccha-*

*romyces cerevisiae* (Gerhardt et al., 1994). These strains were incubated at 30° C. for 24 hour while being shaken with a Shaking incubator.

3. Illumination of ultraviolet ray

One milliliter of the strains cultured for 24 hours was diluted in sterilized water. Then, *Bacillus subtilis* (Gram+) or *Escherichia. coli* (Gram−) (each 0.1 ml) was inoculated in nutrient solid medium (yeast extract 3 g, bacto-peptone 5 g, sodium chloride 8 g, agar 15 g/D.W.11), while *Saccharomyces cerevisiae* (yeast) was inoculated in YPD yeast extract 3 g, bacto-peptone 10 g, dextrose 30 g, agar 15 g/D.W. 11). The inoculated agar plate was illuminated under 50 cm from ultraviolet lamp of clean bench (115V, 30 W, 2537 Å). The colonies of *Escherichia. coli* (Gram−) and *Bacillus subtlis* (Gram+) were illuminated for 40 and 60 seconds, while *Saccharomyces cerevisiae* for 30 and 60 seconds. Ultraviolet ray on the clean bench was measured by photometer (Licon LI-189). As a control, the number of colonies in the medium without ultraviolet ray irradiation was used.

4. Distribution of Hemolytic microorganisms

In order to confirm the colonies of hemolytic microorganisms, known as pathogenic bacteria, which exists in jade powder and jade water, it was counted by using blood agar plate (BAP). After sterilizing blood agar plate (Trypticase soy agar (BBL) 40 g/D.W. 1), the plate was cooled to 48°–50° C. Then, sterile non-fibrous sheep blood was added thereto. Jade powder or jade water was added to the blood agar medium to incubate at 37° C. for 24 hours. The type of the colonies and attributes of hemolytes were examined.

α hemolyte: green ring appears around the colony

β hemolyte: completely clear hemolyte ring appears around the colony

γ hemolyte: no hemolytic effect appears

5. Microbiological analysis

A. Effect of jade water and jade powder concentration

To determine whether any of the microorganism had adapted to jade water and jade powder, the strains were inoculated on nutrient agar plate and YPD that had been adjusted to 10%, 25%, 50%, 100% (v/v) with the jade water and 5%, 10%, 20%, 30% (w/v) with the jade powder. The colonies of *Escherichia. coli* (Gram−), *Bacillus subtilis* (Gram+) and *Saccharomyces cerevisiae* were incubated at 37° C. for 24 hours and 30° C. for 24 hours, respectively.

B. UV shielding effect

UV shielding effect was determined whether growth would occur at the various time of UV illumination. The strains were inoculated on nutrient agar plate that had been adjusted to 10%, 25%, 50%, 100% (v/v) with the jade water and 5%, 10%, 20%, 30% (w/v) with the jade powder. The agar plate was illuminated by ultraviolet lamp of clean bench (115V, 30W, 2537A). The colonies of *Escherichia. coli* and *Bacillus subtilis* were incubated at 37° C. for 24 hours in nutrient solid medium, while that of *Saccharomyces cerevisiae* were incubated at 30° C. for 24 hours in YPD. The numbers of microorganisms were counted with CFU (colony forming unit)/ml.

Results

1. Hemolytic microorganism

Hemolytic property is divided into two groups, i.e. α-type and β-type. γ-Type means non-hemolytic. In case of α-hemolyte, oxyhemoglobin has been altered to methemoglobin, so that a green ring is formed around the colony. In case of β-hemolyte, a completely clear hemolyte ring appears around the colony. Hemolyte is originated from hemolyte toxin. In case of jade powder, β-hemolyte was average 930 CFU/ml, γ-hemolyte 190 CFU/ml. In case of jade water, β-hemolyte was 30 CFU/ml, γ-hemolyte 730 CFU/ml. The presumed reason why relatively more β-hemolytic microorganisms have been detected in jade powder than in jade water is because jade water was collected by double boiling with jade powder.

2. Measurement of colonies of microorganism4

Nutrient broth medium and YPD medium were mixed with jade water of 10%, 25%, 50% and 100%, respectively. The jade powder was mixed in the amount of 5%, 10%, 20% and 30%, respectively, and then incubated. The results were compared with the control group which did not include jade product. In colonies of *Bacillus subtilis* and *Saccharomyces cerevisiae* were similar number with the control, but the number of *Escherichia. coli* which were cultured with jade water of 10%, 25% and 50% were more than that of the control. These results suggest that trace element in jade water affected on the growth of *Escherichia. coli*, but did not affected on the growth of *Bacillus subtilis* and *Saccharomyces cerevisiae*. Thus, the determination of the type and amount of the trace elements in jade water must be performed prior to the study of the phenomenon related to microbial growth. In the jade powder, the numbers of *Bacillus subtilis*, *Escherichia. coli*, and *Saccharomyces cerevisiae* were less than that of control. As increasing the concentrations of the jade powder in the medium, the numbers of microflora were decreased.

3. UV shielding effect

The microorganisms of the normal flora of the skin can be characterized as either transients or residents. Although the resident microflora remains more or less constant, various factors can affect the nature and extent of the normal flora. The weather may cause an increase in temperature and humidity, which increase the density of the skin microflora. Age has an effect that young children have a more varied microflora and carry more gram negative bacteria and potential pathogens than adults. Thus, to determine the effect of jade products on the strength of ultraviolet ray were selected transients microflora as continually being inoculated onto the skin, *Bacillus subtilis* (gram positive bacteria) and *Escherichia coli* as intestinal organisms are continually inoculated onto the surface of the skin by fecal contamination.

The UV shielding effect of jade powder and jade water has been confirmed by the UV sensitivity of microorganisms. The survival rate of *Bacillus subtilis* as cultured at 20% and 30% of jade powder was 23% and 13%, respectively, while illuminated by ultraviolet for 40 seconds, which was higher than the control group (12%) not containing jade powder. In case of using jade water, the survival rate showed similar tendency. The survival rate of *Escherichia. coli* was greater than that of other microorganisms. It was average 74% in case of jade water, and 82% in case of jade powder. In case of liquid medium having 10% concentration of jade powder, the highest survival rate (90%) appeared. The UV shielding effect of jade powder was higher than that of jade water, regardless of the type of microorganisms.

The sensitivity of UV ray is generally decreased in order of gram negative bacteria, yeast, spore forming bacteria and fungi. Also, the sterilization effects and photoreactivation are generally varied dependent upon the species, physiological activity, enzyme and environmental material. The maximum sterilization effect is shown at 260 nm wavelength of UV ray. Many pathogens including *E. coli* and Salmonella were sterilized in 10 minute by 15W ultraviolet lamp according to literature. In case of *Cryptococcus neoformans*, morphology change and cytoplasmic element abnormality was increased with irradiation time of UV ray, after the time lapse of 10 minutes. The sensitivity of ultraviolet ray was decreased in order of *Bacillus subtilis*, *Saccharomyces cerevisiae*, *Escherichia. coli*. In other words, UV shielding effect was in order of *Escherichia. coli*, *Saccharomyces cerevisiae* and *Bacillus subtilis*. As considering the results of growth yield due to jade powder and jade water (the growth of E. coli was the fastest on the jade product medium), E. coli, having large individual numbers, has the highest UV shielding effect. The disinfection effects of sunlight and predacious microorganisms on enteric bacteria E. coli and Proteus vulgaris were examined in sewage water. The effect was proportional to the light intensity and proved to be due to the action of the visible light of short wavelength, no UV light. In this regards, further studies on the sterilization effect by sunlight should be performed.

Conclusion

1. In case of jade powder, β-hemolyte was average 930 CFU/ml, γ-hemolyte 190 CFU/ml. In case of jade water, β-hemolyte was 30 CFU/ml, γ-hemolyte 730 CFU/ml.

2. The size of colony grown in a culture medium containing jade powder and jade water tend to be changed by the concentration of jade powder, rather than that of jade water.

3. From the analysis of number of microorganisms survived after the UV illumination, UV shielding effect in the liquid medium containing jade powder was higher than that containing jade water.

4. The order of UV shielding effect was E. coli, Saccharomyces cerevisiae, Bacillus subtilis.

As can be seen from the above results, the jade powder used in the matrix of the present invention shows excellent UV shielding effect.

Experimental Example 12

The experiment is to investigate the effect of jade containing tiles and supernatant jade water after precipitation of jade powder on the reproduction and growth in rats when jade tiles were placed on the cage and jade water was fed instead of tap water. It was performed by Korea Food Research Institute. The details are described below.

Thirty male and female Sprague Dawley rats (9 week old) were assigned to each treatment. Rats of group A were housed in the cages placed with jade tile and provided with tap water. Rats of group B were fed with supernatant jade water after precipitation of jade powder (2 mg/ml tap water), but no jade tile was placed on the cage. The rats of group C formed a control group (no jade tiles and no jade water). Rats were mated for nine days and then male rats separated and sacrificed for sperm concentration and motility tests. The results are shown in the following Table.

Effects of Jade Products on the Reproduction and Growth of Rats

| Group | A | B | C |
|---|---|---|---|
| Parturition (No. of rats) | 9 | 9 | 8 |
| Litter size (♂/♀) | 96 (57/39) | 94 (57/37) | 102 (54/48) |
| Litter size (head/♀ rat) | 11.8 ± 1.9 | 10.9 ± 1.4 | 12.8 ± 2.1 |
| Body weight at birth (g) | 4.73 ± 1.10 | 5.79 ± 0.95 | 5.35 ± 0.35 |
| Mortality (No. of head) | 4 | 4 | 3 |
| Days from mating to parturition | 23.8 ± 1.4 (n = 10) | 25.1 ± 1.7 (n = 9) | 25.5 ± 3.7 (n = 8) |
| Body weight at weaning (g) | 43.45 ± 8.04 | 42.73 ± 8.76 | 42.07 ± 10.71 |
| Body weight at slaughter (g) | 294.0 ± 10.9 | 274.4 ± 8.6 | 288.4 ± 26.7 |
| Testis weight (g) | 3.90 ± 0.21 | 3.57 ± 0.30 | 3.99 ± 0.15 |
| Sperm concentration ($10^8$/ml) | 6.32 ± 2.4 | 4.80 ± 1.3 | 4.60 ± 1.9 |
| Sperm motility (%) | 91.0 ± 4.2 | 92.0 ± 2.7 | 88.0 ± 7.6 |

From the findings, jade tile and jade water treatments had shown better parturition records. Parturition rates of groups A and B (90%) were higher than those of C (80%), although rats of group C gave birth to several more puppies. Also a length of time from mating to parturition was shorter in group A rats than the other two group rats. Besides these findings, sperm concentration and motility in both rats of group A and B were superior to C. However, the effects of both jade tile and jade water treatments at the same time were not investigated in this study.

In conclusion, the results suggest that jade tile and jade water seem to affect the reproduction and growth of rats: either jade tile or jade water treatment groups had shown better indices of reproduction and growth. It would be very valuable to investigate these effects further more for future application. These findings may be applied as a basic data to the improvement of reproductive efficiency and strengthen the sperm concentration and motility rate.

Experimental Example 13

The experiment is to investigate the relieving effect of jade on the symptoms of diabetes mellitus when various jade products were applied to streptozotocin-induced diabetes mellitus rats. It was performed by Korea Food Research Institute. The details are described below.

To thirty-two(32) Sprague Dawley rats weighing 252–294 g were given streptozotocin (35–40 mg dissolved in 0.1M citrate buffer of pH 4.0) peritoneally. Seven days after administration of streptozotocin, rats showing blood glucose level higher than 250 mg/dl were selected based on uropaper (Eiken Chemical Co., Ltd., Japan). Four experimental groups of 5 rats each were employed for 50 days of experimental period. Group A rats were injected with 1.0 ml of distilled jade water peritoneally (pH 6.4) each day. Rats of group B were housed in cages placed with jade tiles on the bottom throughout the experiment. Rats of group C were fed with supernatant jade water after precipitation of jade powder out as a drinking water everyday. Group D rats as a control did not have any treatment. Diets fed were commercial rat chow, and the rats were cared according to the general practices. Rats were sacrificed on day 50 and blood was collected from abdominal aorta. Plasma were prepared from centrifuging blood containing heparin at 5,000 rpm for 15 min after leaving blood at room temperature for 30 min. Organs (liver, kidney) taken out were weighed and recorded. Measurements tested in blood plasma were HBA (plasma β-hydroxybutyrate), FFA (free fatty acids), cholesterol, HDL-cholesterol and triglyceride. The content of HBA is quantitavely analyzed by measuring the increase of Absorbance (OD) of NADH, which is produced by oxidation by β-hydroxybutyrate dehydrogenase, at 340 nm. Lipids in blood were measured by using a clinical kit (Eiken Chemical Co., Ltd., Japan).

Effects of Jade Products on the Body and Organ Weight Changes in Streptozotocin-Induced Diabetic Rats

| | Body weight (g) | | Organ weight (g/100 g body wt.) | |
|---|---|---|---|---|
| Group | Beginning | Ending | Liver | Kidney |
| A | 270.4 ± 11.3 | 271.7 ± 49.4 | 4.31 ± 0.33 | 1.02 ± 0.12 |
| B | 284.8 ± 6.1 | 279.6 ± 20.4 | 4.30 ± 0.64 | 1.01 ± 0.18 |
| C | 280.4 ± 13.2 | 315.7 ± 41.1 | 3.96 ± 0.75 | 0.87 ± 0.14 |
| D | 257.2 ± 4.2 | 194.8 ± 26.3 | 4.37 ± 0.19 | 0.78 ± 0.04 |

Effects of Jade Products on the Changes of Biochemical Indices in
Streptozotocin-Induced Diabetic Rats

| Group | Glucose (mg/100 ml) | HBA[a] ($\mu$mol/ml) | FFA[b] ($\mu$eq/ml) | TC[c] (mg/100 ml) | TG[d] (mg/100 ml) | HDL[e] (mg/100 ml) |
|---|---|---|---|---|---|---|
| A | 639.2 ± 99.0[a] | 0.782 ± 0.481[a] | 507.6 ± 226.6[a] | 166.2 ± 69.4 | 410.7 ± 50.1 | 32.35 ± 5.94 |
| B | 495.1 ± 228.1[ab] | 0.527 ± 0.296[ab] | 349.5 ± 79.2[ab] | 161.3 ± 45.3 | 122.5 ± 43.5 | 29.49 ± 1.71 |
| C | 354.1 ± 154.2[bc] | 0.425 ± 0.172[ab] | 287.3 ± 71.7[b] | 145.4 ± 29.1 | 87.9 ± 29.2 | 30.55 ± 8.28 |
| D | 196.8 ± 16.3[d] | 0.276 ± 0.036[b] | 291.0 ± 131.2[b] | 158.2 ± 12.2 | 86.8 ± 3.4 | 31.37 ± 3.84 |

$p < 0.05$
[a]$\beta$-hydoxybutyrate (ketone form)
[b]Free fatty acid
[c]Total-cholesterol
[d]Triglyceride (neutral lipid)
[e]High-density lipoprotein cholesterol In terms of body weight, group C rats fed with jade water had shown higher body weight than other groups, of which the body weight was reduced (B, D) or maintained (A) at the end of the experiment. Kidney weights are generally increased in DM patients, and this tendency also was observed in this experiment. Kidney weight of group C was the lowest among the treatments besides control. Liver weight was increased too, but liver weight was the lowest in rats fed with jade water. Concentrations of blood glucose, ketone body and FFA were higher in the order of groups A, B, C and D. Blood plasma cholesterol and triglyceride concentration had followed the same tendency (A>B>C>D) to the above parameters mentioned. From the results, rats fed with jade water (group C) showed comparatively lower values of all the parameters measured rather than the other two experimental groups, and blood cholesterol and FFA concentrations were lower in rats of group C than control without any jade treatment.

TC and TG concentration was in the order of A>B>C>D. The result of glycemic index by blood sugar reaction after meal alters dependent upon the researchers. However, in the experiment, though commercial blended feed was fed without considering glycemic index of cereals, C group fed with jade water showed an effect for alleviating hyperlipidemia, one of diabetic symptoms. There occurred no difference of HDL-cholesterol concentration between the test groups.

The administration of jade water to Streptozotocin-induced diabetic rats showed effects of preventing the reduction of body weight, preventing enlargement of kidney or liver as well as alleviating hyperlipidemia, one of diabetic symptoms.

What is claimed is:

1. A matrix of a powdery mixture containing 5–15% by weight of nephrite jade powder having a particle size of 100–300 mesh, wherein the jade comprises cryptocrystalline tremolite grains, has $\sigma^{18}O$ and has a composition in weight % as follows:

| Silicon | 34 | Tin | 0.024 |
|---|---|---|---|
| Magnesium | 10 | Beryllium | 0.00072 |
| Calcium | 4.9 | Silver | 0.0013 |
| Iron | 0.23 | Titanium | 0.0038 |
| Aluminum | 0.16 | Nickel | 0.0028 |
| Copper | 0.17 | Chromium | 0.0030 |
| Cobalt | 0.046 | Other element | 0 |
| Manganese | 0.14 | | |

2. A matrix of a synthetic glass or a solid mass containing 5–10% by weight of nephrite jade powder having a particle size of 10–200 mesh, wherein the jade comprises cryptocrystalline tremolite grains, has $\sigma^{18}O$ and has a composition in weight % as follows:

| Silicon | 34 | Tin | 0.024 |
|---|---|---|---|
| Magnesium | 10 | Beryllium | 0.00072 |
| Calcium | 4.9 | Silver | 0.0013 |
| Iron | 0.23 | Titanium | 0.0038 |
| Aluminum | 0.16 | Nickel | 0.0028 |
| Copper | 0.17 | Chromium | 0.0030 |
| Cobalt | 0.046 | Other element | 0 |
| Manganese | 0.14 | | |

\* \* \* \* \*